(12) United States Patent
Parker et al.

(10) Patent No.: US 11,324,427 B2
(45) Date of Patent: May 10, 2022

(54) METHOD AND APPARATUS FOR MEASUREMENT OF NEURAL RESPONSE

(71) Applicant: Saluda Medical Pty Ltd., Artarmon (AU)

(72) Inventors: John Louis Parker, Artarmon (AU); Peter Scott Vallack Single, Artarmon (AU); Dean Michael Karantonis, Artarmon (AU)

(73) Assignee: Saluda Medical Pty Ltd, Artarmon (AU)

( * ) Notice: Subject to any disclaimer, the term of this patent is extended or adjusted under 35 U.S.C. 154(b) by 314 days.

(21) Appl. No.: 16/391,181

(22) Filed: Apr. 22, 2019

(65) Prior Publication Data
US 2019/0307341 A1    Oct. 10, 2019

Related U.S. Application Data

(63) Continuation of application No. 15/184,787, filed on Jun. 16, 2016, now Pat. No. 10,278,600, which is a (Continued)

(30) Foreign Application Priority Data

May 13, 2011    (AU) ............................... 2011901817

(51) Int. Cl.
*A61B 5/24*    (2021.01)
*A61N 1/36*    (2006.01)
(Continued)

(52) U.S. Cl.
CPC .............. *A61B 5/24* (2021.01); *A61B 5/4848* (2013.01); *A61B 5/6846* (2013.01); (Continued)

(58) Field of Classification Search
CPC ....... A61B 5/24; A61B 5/4848; A61B 5/6846; A61B 5/7285; A61B 5/7203; (Continued)

(56) References Cited

U.S. PATENT DOCUMENTS 3,724,467 A    4/1973 Avery et al.
3,736,434 A    5/1973 Darrow
(Continued)

FOREIGN PATENT DOCUMENTS

AU    2013277009 B2    1/2016
CN    103648583 A    3/2014
(Continued)

OTHER PUBLICATIONS

Japanese Office Action for Application No. 2017-553090, dated Mar. 16, 2020, 12 pages with English translation.
(Continued)

*Primary Examiner* — Patrick Fernandes
(74) *Attorney, Agent, or Firm* — Fish & Richardson P.C.

(57) ABSTRACT

A method for measuring a neural response to a stimulus. Measurement circuitry is settled prior to a stimulus, by connecting a sense electrode to the measurement circuitry to allow the measurement circuitry to settle towards a bioelectrically defined steady state. Charge is recovered on stimulus electrodes by short circuiting the stimulus electrodes to each other. An electrical stimulus is then applied from the stimulus electrodes to neural tissue, while keeping the sense electrode disconnected from the measurement circuitry. After the stimulus, a delay is imposed during which the stimulus electrodes are open circuited and the sense electrode is disconnected from the measurement circuitry and from the stimulus electrodes. After the delay, a neural response signal present at the sense electrode is measured by connecting the sense electrode to the measurement circuitry.

10 Claims, 23 Drawing Sheets

Related U.S. Application Data continuation of application No. 14/117,144, filed as application No. PCT/AU2012/000511 on May 11, 2012, now Pat. No. 9,386,934.

(51) Int. Cl.
*A61B 5/00* (2006.01)
*A61M 5/172* (2006.01)

(52) U.S. Cl.
CPC ......... *A61B 5/7285* (2013.01); *A61M 5/1723* (2013.01); *A61N 1/36071* (2013.01); *A61N 1/36125* (2013.01); *A61N 1/36135* (2013.01); *A61N 1/36146* (2013.01); *A61B 5/7203* (2013.01); *A61M 2230/08* (2013.01)

(58) Field of Classification Search
CPC .. A61B 5/4836; A61B 5/4041; A61M 5/1723; A61M 2230/08; A61N 1/36071; A61N 1/36125; A61N 1/36135; A61N 1/36146; A61N 1/0551; A61N 1/36185; A61N 1/36139

See application file for complete search history.

(56) References Cited

U.S. PATENT DOCUMENTS

| | | |
|---|---|---|
| 3,817,254 A | 6/1974 | Maurer |
| 3,898,472 A | 8/1975 | Long |
| 4,158,196 A | 6/1979 | Crawford, Jr. |
| 4,418,695 A | 12/1983 | Buffet |
| 4,474,186 A | 10/1984 | Ledley et al. |
| 4,628,934 A | 12/1986 | Pohndorf et al. |
| 4,807,643 A | 2/1989 | Rosier |
| 4,856,525 A | 8/1989 | van den Honert |
| 5,113,859 A | 5/1992 | Funke |
| 5,139,020 A | 8/1992 | Koestner et al. |
| 5,143,081 A | 9/1992 | Young et al. |
| 5,156,154 A | 10/1992 | Valenta, Jr. et al. |
| 5,172,690 A | 12/1992 | Nappholz et al. |
| 5,184,615 A | 2/1993 | Nappholz et al. |
| 5,188,106 A | 2/1993 | Nappholz et al. |
| 5,215,100 A | 6/1993 | Spitz |
| 5,324,311 A | 6/1994 | Acken |
| 5,417,719 A | 5/1995 | Hull et al. |
| 5,431,693 A | 7/1995 | Schroeppel |
| 5,458,623 A | 10/1995 | Lu et al. |
| 5,476,486 A | 12/1995 | Lu et al. |
| 5,497,781 A | 3/1996 | Chen et al. |
| 5,638,825 A | 6/1997 | Yamazaki et al. |
| 5,702,429 A | 12/1997 | King et al. |
| 5,758,651 A | 6/1998 | Nygard et al. |
| 5,776,170 A | 7/1998 | Macdonald et al. |
| 5,785,651 A | 7/1998 | Kuhn et al. |
| 5,792,212 A | 8/1998 | Weijand et al. |
| 5,814,092 A | 9/1998 | King |
| 5,895,416 A | 4/1999 | Barreras et al. |
| 5,913,882 A | 6/1999 | King |
| 5,999,848 A | 12/1999 | Gord et al. |
| 6,020,857 A | 2/2000 | Podger |
| 6,027,456 A | 2/2000 | Feler et al. |
| 6,038,480 A | 3/2000 | Hrdlicka et al. |
| 6,066,163 A | 5/2000 | John |
| 6,114,164 A | 9/2000 | Dennis et al. |
| 6,144,881 A | 11/2000 | Hemming et al. |
| 6,157,861 A | 12/2000 | Faltys et al. |
| 6,212,431 B1 | 4/2001 | Hahn et al. |
| 6,246,912 B1 | 6/2001 | Sluijter et al. |
| 6,381,496 B1 | 4/2002 | Meadows et al. |
| 6,449,512 B1 | 9/2002 | Boveja |
| 6,463,328 B1 | 10/2002 | John |
| 6,473,649 B1 | 10/2002 | Gryzwa et al. |
| 6,473,653 B1 | 10/2002 | Schallhorn et al. |
| 6,493,576 B1 | 12/2002 | Dankwart-Eder |
| 6,516,227 B1 | 2/2003 | Meadows et al. |
| 6,522,932 B1 | 2/2003 | Kuzma |
| 6,600,955 B1 | 7/2003 | Zierhofer et al. |
| 6,658,293 B2 | 12/2003 | Vonk et al. |
| 6,675,046 B2 | 1/2004 | Holsheimer |
| 6,782,292 B2 | 8/2004 | Whitehurst |
| 6,895,280 B2 | 5/2005 | Meadows et al. |
| 6,898,582 B2 | 5/2005 | Lange et al. |
| 6,909,917 B2 | 6/2005 | Woods et al. |
| 7,089,059 B1 | 8/2006 | Pless |
| 7,171,261 B1 | 1/2007 | Litvak et al. |
| 7,177,675 B2 | 2/2007 | Suffin et al. |
| 7,206,640 B1 | 4/2007 | Overstreet |
| 7,231,254 B2 | 6/2007 | DiLorenzo et al. |
| 7,286,876 B2 | 10/2007 | Yonce et al. |
| 7,412,287 B2 | 8/2008 | Yonce et al. |
| 7,450,992 B1 | 11/2008 | Cameron |
| 7,634,315 B2 | 12/2009 | Cholette |
| 7,734,340 B2 | 6/2010 | De Ridder |
| 7,742,810 B2 | 6/2010 | Moffitt |
| 7,792,584 B2 | 9/2010 | Van et al. |
| 7,818,052 B2 | 10/2010 | Litvak et al. |
| 7,831,305 B2 | 11/2010 | Gliner |
| 7,835,804 B2 | 11/2010 | Fridman et al. |
| 7,890,182 B2 | 2/2011 | Parramon et al. |
| 7,894,905 B2 | 2/2011 | Pless et al. |
| 8,190,251 B2 | 5/2012 | Molnar et al. |
| 8,224,459 B1 | 7/2012 | Pianca et al. |
| 8,239,031 B2 | 8/2012 | Fried et al. |
| 8,249,698 B2 | 8/2012 | Mugler et al. |
| 8,359,102 B2 | 1/2013 | Thacker et al. |
| 8,417,342 B1 | 4/2013 | Abell |
| 8,494,645 B2 | 7/2013 | Spitzer et al. |
| 8,515,545 B2 | 8/2013 | Trier |
| 8,538,541 B2 | 9/2013 | Milojevic et al. |
| 8,588,929 B2 | 11/2013 | Davis et al. |
| 8,620,459 B2 | 12/2013 | Gibson et al. |
| 8,655,002 B2 | 2/2014 | Parker |
| 8,670,830 B2 | 3/2014 | Carlson et al. |
| 8,886,323 B2 | 11/2014 | Wu et al. |
| 8,945,216 B2 | 2/2015 | Parker et al. |
| 9,044,155 B2 | 6/2015 | Strahl |
| 9,155,892 B2 | 10/2015 | Parker et al. |
| 9,302,112 B2 | 4/2016 | Bornzin et al. |
| 9,381,356 B2 | 7/2016 | Parker et al. |
| 9,386,934 B2 | 7/2016 | Parker et al. |
| 9,566,439 B2 | 2/2017 | Single et al. |
| 9,872,990 B2 | 1/2018 | Parker et al. |
| 9,974,455 B2 | 5/2018 | Parker et al. |
| 10,206,596 B2 | 2/2019 | Single et al. |
| 10,278,600 B2 | 5/2019 | Parker et al. |
| 10,368,762 B2 | 8/2019 | Single |
| 10,426,409 B2 | 10/2019 | Single |
| 10,500,399 B2 | 12/2019 | Single |
| 10,568,559 B2 | 2/2020 | Parker et al. |
| 10,588,524 B2 | 3/2020 | Single et al. |
| 10,588,698 B2 | 3/2020 | Parker et al. |
| 10,632,307 B2 | 4/2020 | Parker |
| 10,842,996 B2 | 11/2020 | Baru et al. |
| 10,849,525 B2 | 12/2020 | Parker et al. |
| 10,894,158 B2 | 1/2021 | Parker |
| 10,918,872 B2 | 2/2021 | Parker et al. |
| 11,006,846 B2 | 5/2021 | Parker et al. |
| 11,006,857 B2 | 5/2021 | Parker |
| 11,045,129 B2 | 6/2021 | Parker et al. |
| 11,110,270 B2 | 9/2021 | Parker et al. |
| 11,167,129 B2 | 11/2021 | Parker |
| 11,172,864 B2 | 11/2021 | Parker et al. |
| 11,179,091 B2 | 11/2021 | Karantonis et al. |
| 11,191,966 B2 | 12/2021 | Wah |
| 2002/0055688 A1 | 5/2002 | Katims |
| 2002/0099419 A1 | 7/2002 | Ayal et al. |
| 2002/0193670 A1 | 12/2002 | Garfield et al. |
| 2003/0032889 A1 | 2/2003 | Wells |
| 2003/0045909 A1 | 3/2003 | Gross et al. |
| 2003/0139781 A1 | 7/2003 | Bradley et al. |
| 2003/0153959 A1 | 8/2003 | Thacker et al. |
| 2003/0195580 A1 | 10/2003 | Bradley et al. |
| 2004/0088017 A1 | 5/2004 | Sharma et al. |
| 2004/0122482 A1 | 6/2004 | Tung et al. |

(56) References Cited

U.S. PATENT DOCUMENTS

| | | |
|---|---|---|
| 2004/0158298 A1 | 8/2004 | Gliner |
| 2004/0225211 A1 | 11/2004 | Gozani et al. |
| 2004/0254494 A1 | 12/2004 | Spokoyny et al. |
| 2005/0010265 A1 | 1/2005 | Baru Fassio |
| 2005/0017190 A1 | 1/2005 | Eversmann et al. |
| 2005/0021104 A1 | 1/2005 | DiLorenzo |
| 2005/0065427 A1 | 3/2005 | Magill |
| 2005/0070982 A1 | 3/2005 | Heruth et al. |
| 2005/0075683 A1 | 4/2005 | Miesel et al. |
| 2005/0101878 A1 | 5/2005 | Daly et al. |
| 2005/0107674 A1 | 5/2005 | Parthasarathy et al. |
| 2005/0113877 A1 | 5/2005 | Giardiello et al. |
| 2005/0137670 A1 | 6/2005 | Christopherson et al. |
| 2005/0149154 A1 | 7/2005 | Cohen |
| 2005/0192567 A1 | 9/2005 | Katims |
| 2005/0203600 A1 | 9/2005 | Wallace |
| 2005/0209655 A1 | 9/2005 | Bradley et al. |
| 2005/0282149 A1 | 12/2005 | Kovacs et al. |
| 2006/0009820 A1 | 1/2006 | Royle et al. |
| 2006/0020291 A1 | 1/2006 | Gozani |
| 2006/0135998 A1 | 6/2006 | Libbus et al. |
| 2006/0195159 A1 | 8/2006 | Bradley et al. |
| 2006/0212089 A1 | 9/2006 | Tass |
| 2006/0217782 A1 | 9/2006 | Boveja et al. |
| 2006/0264752 A1 | 11/2006 | Rubinsky et al. |
| 2006/0287609 A1 | 12/2006 | Litvak et al. |
| 2007/0021800 A1 | 1/2007 | Bradley et al. |
| 2007/0073354 A1 | 3/2007 | Knudson et al. |
| 2007/0100378 A1 | 5/2007 | Maschino |
| 2007/0178579 A1 | 8/2007 | Ross et al. |
| 2007/0185409 A1 | 8/2007 | Wu et al. |
| 2007/0208394 A1 | 9/2007 | King et al. |
| 2007/0225765 A1 | 9/2007 | King |
| 2007/0225767 A1 | 9/2007 | Daly et al. |
| 2007/0244410 A1 | 10/2007 | Fridman et al. |
| 2007/0250120 A1 | 10/2007 | Flach et al. |
| 2007/0255372 A1 | 11/2007 | Metzler et al. |
| 2007/0282217 A1 | 12/2007 | McGinnis et al. |
| 2007/0287931 A1 | 12/2007 | Dilorenzo |
| 2008/0021292 A1 | 1/2008 | Stypulkowski |
| 2008/0051647 A1 | 2/2008 | Wu et al. |
| 2008/0064947 A1 | 3/2008 | Heruth et al. |
| 2008/0077191 A1 | 3/2008 | Morrell |
| 2008/0097529 A1 | 4/2008 | Parramon et al. |
| 2008/0132964 A1 | 6/2008 | Cohen et al. |
| 2008/0147155 A1 | 6/2008 | Swoyer |
| 2008/0183076 A1 | 7/2008 | Witte et al. |
| 2008/0208304 A1 | 8/2008 | Zdravkovic et al. |
| 2008/0234780 A1 | 9/2008 | Smith et al. |
| 2008/0275527 A1 | 11/2008 | Greenberg et al. |
| 2008/0294221 A1 | 11/2008 | Kilgore |
| 2008/0300655 A1 | 12/2008 | Cholette |
| 2008/0319508 A1 | 12/2008 | Botros et al. |
| 2009/0030337 A1 | 1/2009 | Gozani et al. |
| 2009/0033486 A1 | 2/2009 | Costantino et al. |
| 2009/0058635 A1 | 3/2009 | Lalonde et al. |
| 2009/0082691 A1 | 3/2009 | Denison et al. |
| 2009/0149912 A1 | 6/2009 | Dacey, Jr. et al. |
| 2009/0157155 A1 | 6/2009 | Bradley |
| 2009/0270957 A1 | 10/2009 | Pianca |
| 2009/0287277 A1 | 11/2009 | Conn et al. |
| 2009/0299214 A1 | 12/2009 | Wu et al. |
| 2009/0306491 A1 | 12/2009 | Haggers |
| 2009/0306533 A1 | 12/2009 | Rousche et al. |
| 2010/0010388 A1 | 1/2010 | Panken et al. |
| 2010/0057159 A1 | 3/2010 | Lozano |
| 2010/0058126 A1 | 3/2010 | Chang et al. |
| 2010/0069835 A1 | 3/2010 | Parker |
| 2010/0069996 A1 | 3/2010 | Strahl |
| 2010/0070007 A1 | 3/2010 | Parker |
| 2010/0070008 A1 | 3/2010 | Parker |
| 2010/0100153 A1* | 4/2010 | Carlson ............... A61N 1/0529 607/45 |
| 2010/0106231 A1 | 4/2010 | Torgerson |
| 2010/0114237 A1 | 5/2010 | Giftakis et al. |
| 2010/0114258 A1 | 5/2010 | Donofrio et al. |
| 2010/0125313 A1 | 5/2010 | Lee et al. |
| 2010/0125314 A1 | 5/2010 | Bradley et al. |
| 2010/0145222 A1 | 6/2010 | Brunnett et al. |
| 2010/0152808 A1 | 6/2010 | Boggs |
| 2010/0179626 A1 | 7/2010 | Pilarski |
| 2010/0191307 A1 | 7/2010 | Fang et al. |
| 2010/0204748 A1 | 8/2010 | Lozano et al. |
| 2010/0222844 A1 | 9/2010 | Troosters et al. |
| 2010/0222858 A1 | 9/2010 | Meloy |
| 2010/0249643 A1 | 9/2010 | Gozani et al. |
| 2010/0249867 A1 | 9/2010 | Wanasek |
| 2010/0258342 A1 | 10/2010 | Parker |
| 2010/0262208 A1 | 10/2010 | Parker |
| 2010/0262214 A1 | 10/2010 | Robinson |
| 2010/0280570 A1 | 11/2010 | Sturm et al. |
| 2010/0286748 A1 | 11/2010 | Midani et al. |
| 2010/0331604 A1 | 12/2010 | Okamoto et al. |
| 2010/0331926 A1 | 12/2010 | Lee et al. |
| 2011/0004207 A1 | 1/2011 | Wallace et al. |
| 2011/0021943 A1 | 1/2011 | Lacour et al. |
| 2011/0028859 A1 | 2/2011 | Chian |
| 2011/0040546 A1 | 2/2011 | Gerber et al. |
| 2011/0077712 A1 | 3/2011 | Killian |
| 2011/0087085 A1 | 4/2011 | Tsampazis et al. |
| 2011/0093042 A1 | 4/2011 | Torgerson et al. |
| 2011/0106100 A1 | 5/2011 | Bischoff |
| 2011/0184488 A1 | 7/2011 | De Ridder et al. |
| 2011/0204811 A1 | 8/2011 | Pollmann-retsch |
| 2011/0224665 A1 | 9/2011 | Crosby et al. |
| 2011/0224749 A1 | 9/2011 | Ben-David et al. |
| 2011/0264165 A1 | 10/2011 | Molnar et al. |
| 2011/0270343 A1 | 11/2011 | Buschman et al. |
| 2011/0307030 A1 | 12/2011 | John |
| 2011/0313310 A1 | 12/2011 | Tomita |
| 2011/0313483 A1 | 12/2011 | Hincapie et al. |
| 2012/0029377 A1 | 2/2012 | Polak |
| 2012/0059275 A1 | 3/2012 | Fagin et al. |
| 2012/0101552 A1 | 4/2012 | Lazarewicz et al. |
| 2012/0101826 A1 | 4/2012 | Visser et al. |
| 2012/0109004 A1 | 5/2012 | Cadwell |
| 2012/0109236 A1 | 5/2012 | Jacobson et al. |
| 2012/0155183 A1 | 6/2012 | Aritome |
| 2012/0185020 A1 | 7/2012 | Simon et al. |
| 2012/0245481 A1 | 9/2012 | Blanco et al. |
| 2012/0253423 A1 | 10/2012 | Youn et al. |
| 2012/0277621 A1 | 11/2012 | Gerber et al. |
| 2012/0277823 A1 | 11/2012 | Gerber et al. |
| 2012/0310301 A1 | 12/2012 | Bennett et al. |
| 2013/0041449 A1 | 2/2013 | Cela et al. |
| 2013/0053722 A1 | 2/2013 | Carlson et al. |
| 2013/0060302 A1 | 3/2013 | Polefko et al. |
| 2013/0172774 A1 | 7/2013 | Crowder et al. |
| 2013/0268043 A1 | 10/2013 | Tasche et al. |
| 2013/0289661 A1 | 10/2013 | Griffith et al. |
| 2013/0289683 A1 | 10/2013 | Parker et al. |
| 2014/0066803 A1 | 3/2014 | Choi |
| 2014/0142447 A1 | 5/2014 | Takahashi et al. |
| 2014/0194771 A1 | 7/2014 | Parker et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243926 A1 | 8/2014 | Carcieri |
| 2014/0243931 A1 | 8/2014 | Parker et al. |
| 2014/0249396 A1 | 9/2014 | Shacham-diamand et al. |
| 2014/0276195 A1 | 9/2014 | Papay et al. |
| 2014/0277250 A1 | 9/2014 | Su et al. |
| 2014/0277267 A1 | 9/2014 | Vansickle et al. |
| 2014/0288551 A1 | 9/2014 | Bharmi et al. |
| 2014/0288577 A1 | 9/2014 | Robinson et al. |
| 2014/0296737 A1 | 10/2014 | Parker et al. |
| 2014/0324118 A1 | 10/2014 | Simon et al. |
| 2014/0350634 A1 | 11/2014 | Grill et al. |
| 2014/0358024 A1 | 12/2014 | Nelson et al. |
| 2015/0018699 A1 | 1/2015 | Zeng et al. |
| 2015/0025597 A1 | 1/2015 | Surth et al. |
| 2015/0126839 A1 | 5/2015 | Li et al. |
| 2015/0148869 A1 | 5/2015 | Dorvall, II et al. |
| 2015/0164354 A1 | 6/2015 | Parker et al. |

(56) References Cited

U.S. PATENT DOCUMENTS

| | | |
|---|---|---|
| 2015/0174396 A1 | 6/2015 | Fisher et al. |
| 2015/0238104 A1 | 8/2015 | Tass |
| 2015/0238304 A1 | 8/2015 | Lamraoui |
| 2015/0282725 A1 | 10/2015 | Single |
| 2015/0313487 A1 | 11/2015 | Single |
| 2015/0360031 A1 | 12/2015 | Bornzin et al. |
| 2015/0374999 A1 | 12/2015 | Parker |
| 2016/0082265 A1 | 3/2016 | Moffitt et al. |
| 2016/0082268 A1 | 3/2016 | Hershey et al. |
| 2016/0101289 A1 | 4/2016 | Stolen et al. |
| 2016/0106980 A1 | 4/2016 | Sürth et al. |
| 2016/0121124 A1 | 5/2016 | Johanek et al. |
| 2016/0129272 A1 | 5/2016 | Hou et al. |
| 2016/0144189 A1 | 5/2016 | Bakker et al. |
| 2016/0166164 A1 | 6/2016 | Obradovic et al. |
| 2016/0175594 A1 | 6/2016 | Min et al. |
| 2016/0287126 A1 | 10/2016 | Parker et al. |
| 2016/0287182 A1 | 10/2016 | Single |
| 2016/0367808 A9 | 12/2016 | Simon et al. |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0173335 A1 | 6/2017 | Min et al. |
| 2017/0173341 A1 | 6/2017 | Johanek et al. |
| 2017/0216587 A1 | 8/2017 | Parker |
| 2017/0361101 A1 | 12/2017 | Single |
| 2018/0071513 A1 | 3/2018 | Weiss et al. |
| 2018/0104493 A1 | 4/2018 | Doan et al. |
| 2018/0110987 A1 | 4/2018 | Parker |
| 2018/0117335 A1 | 5/2018 | Parker et al. |
| 2018/0132747 A1 | 5/2018 | Parker et al. |
| 2018/0132760 A1 | 5/2018 | Parker |
| 2018/0133459 A1 | 5/2018 | Parker et al. |
| 2018/0228391 A1 | 8/2018 | Parker et al. |
| 2018/0228547 A1 | 8/2018 | Parker |
| 2018/0229046 A1 | 8/2018 | Parker et al. |
| 2018/0256052 A1 | 9/2018 | Parker et al. |
| 2019/0001139 A1 | 1/2019 | Mishra et al. |
| 2019/0030339 A1 | 1/2019 | Baru et al. |
| 2019/0125269 A1 | 5/2019 | Markovic et al. |
| 2019/0168000 A1 | 6/2019 | Laird-wah |
| 2019/0216343 A1 | 7/2019 | Single et al. |
| 2019/0239768 A1 | 8/2019 | Karantonis et al. |
| 2019/0357788 A1 | 11/2019 | Single |
| 2020/0029914 A1 | 1/2020 | Single |
| 2020/0129108 A1 | 4/2020 | Parker et al. |
| 2020/0155240 A1 | 5/2020 | Parker et al. |
| 2020/0215331 A1 | 7/2020 | Single |
| 2020/0282208 A1 | 9/2020 | Parker |
| 2021/0001133 A1 | 1/2021 | Williams et al. |
| 2021/0016091 A1 | 1/2021 | Parker et al. |
| 2021/0121696 A1 | 4/2021 | Parker et al. |
| 2021/0162214 A1 | 6/2021 | Parker |
| 2021/0267518 A1 | 9/2021 | Parker et al. |
| 2021/0308449 A1 | 10/2021 | Parker |
| 2021/0315502 A1 | 10/2021 | Parker et al. |
| 2021/0379386 A1 | 12/2021 | Parker et al. |
| 2021/0387005 A1 | 12/2021 | Parker et al. |
| 2021/0387008 A1 | 12/2021 | Single |

FOREIGN PATENT DOCUMENTS

| | | |
|---|---|---|
| CN | 103654762 A | 3/2014 |
| CN | 103842022 A | 6/2014 |
| CN | 104411360 A | 3/2015 |
| EP | 0219084 | 4/1987 |
| EP | 1244496 A1 | 10/2002 |
| EP | 0998958 B1 | 8/2005 |
| EP | 2019716 A | 11/2007 |
| EP | 2243510 A2 | 10/2010 |
| EP | 2443995 A2 | 4/2012 |
| EP | 2520327 A2 | 11/2012 |
| EP | 2707095 A1 | 3/2014 |
| EP | 3229893 A1 | 10/2017 |
| JP | 2006504494 A | 2/2006 |
| JP | 2009512505 A | 3/2009 |
| JP | 2012524629 | 10/2012 |
| JP | 2013500779 A | 1/2013 |
| JP | 2013527784 A | 7/2013 |
| JP | 2013536044 A | 9/2013 |
| JP | 2014522261 A | 9/2014 |
| JP | 2014523261 A | 9/2014 |
| WO | 1983003191 A | 9/1983 |
| WO | 1993001863 A1 | 2/1993 |
| WO | 1996012383 A1 | 4/1996 |
| WO | 2000002623 A1 | 1/2000 |
| WO | 2002036003 A1 | 11/2001 |
| WO | 2002038031 | 5/2002 |
| WO | 2002049500 A2 | 6/2002 |
| WO | 2003028521 A2 | 4/2003 |
| WO | 2003043690 | 5/2003 |
| WO | 2003103484 | 12/2003 |
| WO | 2004021885 A1 | 3/2004 |
| WO | 2004103455 | 12/2004 |
| WO | 2005032656 A1 | 4/2005 |
| WO | 2005105202 A1 | 11/2005 |
| WO | 2005122887 A2 | 12/2005 |
| WO | 2006091636 A2 | 8/2006 |
| WO | 2007050657 A1 | 5/2007 |
| WO | 2007064936 A1 | 6/2007 |
| WO | 2007127926 A2 | 11/2007 |
| WO | 2007130170 A1 | 11/2007 |
| WO | 2008004204 A1 | 1/2008 |
| WO | 2008049199 A1 | 5/2008 |
| WO | 2009002072 A2 | 12/2008 |
| WO | 2009002579 A1 | 12/2008 |
| WO | 2009010870 A2 | 1/2009 |
| WO | 2009130515 A2 | 10/2009 |
| WO | 2009146427 A1 | 12/2009 |
| WO | 2010013170 A1 | 2/2010 |
| WO | 2010044989 A2 | 4/2010 |
| WO | 2010051392 A1 | 5/2010 |
| WO | 2010051406 A1 | 5/2010 |
| WO | 2010057046 A2 | 5/2010 |
| WO | 2010124139 A1 | 10/2010 |
| WO | 2010138915 A1 | 12/2010 |
| WO | 2011011327 A1 | 1/2011 |
| WO | 2011014570 A1 | 2/2011 |
| WO | WO 2011017778 | 2/2011 |
| WO | 2011066477 A1 | 6/2011 |
| WO | 2011066478 A1 | 6/2011 |
| WO | 2011112843 A1 | 9/2011 |
| WO | 2011119251 A2 | 9/2011 |
| WO | 2011159545 A2 | 12/2011 |
| WO | 2012027252 A2 | 3/2012 |
| WO | 2012027791 A1 | 3/2012 |
| WO | 2012155183 A1 | 11/2012 |
| WO | 2012155184 A1 | 11/2012 |
| WO | 2012155185 A1 | 11/2012 |
| WO | 2012155187 A1 | 11/2012 |
| WO | 2012155188 A1 | 11/2012 |
| WO | 2012155189 A1 | 11/2012 |
| WO | 2012155190 A1 | 11/2012 |
| WO | 2012162349 A1 | 11/2012 |
| WO | 2013063111 A1 | 5/2013 |
| WO | 2013075171 A1 | 5/2013 |
| WO | 2014071445 A1 | 5/2014 |
| WO | 2014071446 A1 | 5/2014 |
| WO | 2014143577 A1 | 9/2014 |
| WO | 2014150001 A1 | 9/2014 |
| WO | 2015070281 A1 | 5/2015 |
| WO | 2015074121 A1 | 5/2015 |
| WO | 2015109239 A1 | 7/2015 |
| WO | 2015143509 A1 | 10/2015 |
| WO | 2015168735 A1 | 11/2015 |
| WO | 2016011512 | 1/2016 |
| WO | 2016048974 A1 | 3/2016 |
| WO | 2016059556 A1 | 4/2016 |
| WO | 2016077882 A1 | 5/2016 |
| WO | 2016090420 A1 | 6/2016 |
| WO | 2016090436 A1 | 6/2016 |
| WO | 2016115596 A1 | 7/2016 |
| WO | 2016161484 A2 | 10/2016 |

(56) References Cited

FOREIGN PATENT DOCUMENTS

| WO | 2016168798 A1 | 10/2016 |
|---|---|---|
| WO | 2016191807 A1 | 12/2016 |
| WO | 2016191808 A1 | 12/2016 |
| WO | 2016191815 A1 | 12/2016 |
| WO | WO 2017053504 | 3/2017 |
| WO | 2017173493 A1 | 10/2017 |
| WO | 2017210352 A1 | 12/2017 |
| WO | 2017219096 A1 | 12/2017 |
| WO | 2018119220 A1 | 6/2018 |
| WO | 2018160992 A1 | 9/2018 |
| WO | 2019178634 A1 | 9/2019 |
| WO | 2019204884 A1 | 10/2019 |
| WO | 2019231796 A1 | 12/2019 |
| WO | 2020082118 A1 | 4/2020 |
| WO | 2020082126 A1 | 4/2020 |
| WO | 2020082128 A1 | 4/2020 |
| WO | 2020087123 A1 | 5/2020 |
| WO | 2020087135 A1 | 5/2020 |
| WO | 2020124135 A1 | 6/2020 |

OTHER PUBLICATIONS

Japanese Office Action for Application No. 2018-513699, dated Jun. 8, 2020, 7 pages with English translation.
Office Action for Chinese Patent Application No. 201680020725.4, dated Mar. 16, 2020, 8 pgs.
International Preliminary Report for International Application No. PCT/AU2019/050384, dated Oct. 27, 2020, 8 pgs.
International Preliminary Report on Patentability for International Application No. PCT/AU2018/050278, dated Sep. 29, 2020, 7 pgs.
International Search Report and Written Opinion for International Application No. PCT/AU2018/050278, Search completed Jun. 18, 2018, dated Jun. 18, 2018, 12 pgs.
International Search Report and Written Opinion for International Application No. PCT/AU2019/050384, Search completed Jun. 25, 2019, dated Jun. 25, 2019, 15 pgs.
Kopelman et al., "Attempted Reversible Sympathetic Ganglion Block by An Implantable Neurostimulator", Interactive Cardiovascular and Thoracic Surgery, Feb. 7, 2012, vol. 14, Issue 5, pp. 605-609, doi:10.1093/icvts/ivr137.
Extended European Search Report for European Application No. 16802237.4, Search completed Dec. 11, 2018, dated Dec. 19, 2018, 9 Pgs.
Extended European Search Report for European Application No. 16802238.2, Search completed Oct. 17, 2018, dated Oct. 24, 2018, 8 Pgs.
International Preliminary Report for International Application No. PCT/AU2017/050296, dated Oct. 9, 2018, 7 Pgs.
International Search Report and Written Opinion for International Application No. PCT/AU2017/050647, Search completed Sep. 29, 2017, dated Sep. 29, 2017, 13 Pgs.
Bahmer et al., "Application of triphasic pulses with adjustable phase amplitude ratio (PAR) for cochlear ECAP recording: I. Amplitude growth functions", Journal of Neuroscience Methods, Clinical Neuroscience, 2012, vol. 205, pp. 202-211.
Bahmer et al., "Effects of electrical pulse polarity shape on intra cochlear neural responses in humans: Triphasic pulses with cathodic second phase", Hearing Research, 2013, vol. 306, pp. 123-130.
De Ridder et al., "Burst Spinal Cord Stimulation toward Paresthesia-Free Pain Suppression", Nuerosurgery-online.com, May 2010, vol. 66, No. 8, pp. 986-990.
Gnadt et al., "Spectral Cancellation of Microstimulation Artifact for Simultaneous Neural Recording In Situ", IEEE Transactions on Biomedical Engineering, Oct. 2003, Date of Publication: Sep. 23, 2003, vol. 50, No. 10, pp. 1129-1135, DOI: 10.1109/TBME.2003. 816077.
International Search Report and Written Opinion for International Application No. PCT/AU2019/051385, Search completed Mar. 24, 2020, dated Mar. 24, 2020, 8 Pgs.

Abrard et al., "A time-frequency blindsignal separation methodapplicable to underdetermined mixtures of dependent sources", Signal Processing 85 (2005) 1389-1403.
Casey et al., "Separation of Mixed Audio Sources by Independent Subspace Analysis", Mitsubishi Electric Research Laboratories (2001).
Jang et al, "Single Channel Signal Separation Using Time-Domain Basis Functions", IEEE Signal Processing Letters, Jun. 2003, vol. 10, No. 6.
Jang et al., "A Maximum Likelihood Approach to Single-channel Source Separation", Journal of Machine Learning Research 4 (2003) 1365-1392.
Laird-Wah, "Improving Spinal Cord Stimulation: Model-Based Approaches to Evoked Response Telemetry", UNSW, Aug. 2015.
Mannan et al., "Identification and Removal of Physiological Artifacts From Electroencephalogram Signals: A Review", IEEE Access, May 31, 2018, vol. 6, pp. 30630-30652, https://doi.org/10.1109/ACCESS.2018.2842082.
Niazy et al., "Removal of FMRI environment artifacts from EEG data using optimal basis sets", NeuroImage 28 (2005) 720-737.
Takahashi et al, "Classification of neuronal activities from tetrode recordings using independent component analysis", Neurocomputing, (2002), vol. 49, Issues 1-4, 289-298.
Zhang et al., "Automatic Artifact Removal from Electroencephalogram Data Based on A Priori Artifact Information", BioMed research international. 2015. 720450. Aug. 25, 2015 DOI: https://doi.org/10.1155/2015/720450.
European Search Report for European Application 12785619.3 Search Completed Oct. 13, 2014, dated Oct. 23, 2014, 7 pgs.
European Search Report for European Application 12785669.8 Search Completed Sep. 22, 2014, dated Sep. 29, 2014, 5 pgs.
European Search Report for European Application No. 15861444.6, Search completed Jul. 13, 2018, dated Jul. 23, 2018, 8 pgs.
Extended European Search Report for EP Application 12785483.4 completed Sep. 16, 2014, 7 pgs.
Extended European Search Report for European Application No. 11820923.8, report completed Dec. 9, 2013, report dated Dec. 17, 2013, 6 pgs.
Extended European Search Report for European Application No. 13852669.4, Search completed Jun. 8, 2016, dated Jun. 22, 2016, 09 Pgs.
Extended European Search Report for European Application No. 14861553.7, Search completed Jun. 8, 2017, dated Jun. 19, 2017, 8 Pgs.
Extended European Search Report for European Application No. 14863597.2, Search completed Jun. 6, 2017, dated Jun. 13, 2017, 9 Pgs.
Extended European Search Report for European Application No. 15768956.3, Search completed Oct. 3, 2017, dated Oct. 10, 2017, 8 Pgs.
Extended European Search Report for European Application No. 16739680.3, Search completed Jun. 1, 2018, dated Jun. 12, 2018, 9 Pgs.
Extended European Search Report for European Application No. 13853514.1, Search completed Jun. 8, 2016, dated Jun. 15, 2016, 07 Pgs.
International Preliminary Report for International Application No. PCT/AU2017/050647, dated Dec. 25, 2018, 8 pgs.
International Preliminary Report on Patentability for International Application No. PCT/AU2011/001127, Report dated Mar. 5, 2013, 9 pgs.
International Preliminary Report on Patentability for International Application No. PCT/AU2012/000511, Report dated Nov. 19, 2013, 6 pgs.
International Preliminary Report on Patentability for International Application No. PCT/AU2012/000512, Report dated Nov. 19, 2013, 8 pgs.
International Preliminary Report on Patentability for International Application No. PCT/AU2012/000513, Report dated Nov. 19, 2013, 11 pgs.
International Preliminary Report on Patentability for International Application No. PCT/AU2012/000515, Report dated Nov. 19, 2013, 5 pgs.

(56) References Cited

OTHER PUBLICATIONS

International Preliminary Report on Patentability for International Application No. PCT/AU2012/000516, Report dated Nov. 19, 2013, 9 pgs.
International Preliminary Report on Patentability for International Application No. PCT/AU2012/000517, Report dated Nov. 19, 2013, 6 pgs.
International Preliminary Report on Patentability for International Application No. PCT/AU2012/000518, Report dated Nov. 19, 2013, 11 pgs.
International Preliminary Report on Patentability for International Application No. PCT/AU2012/001441, Report dated May 27, 2014, 10 pgs.
International Preliminary Report on Patentability for International Application No. PCT/AU2013/001279, Report dated May 12, 2015, 6 pgs.
International Preliminary Report on Patentability for International Application No. PCT/AU2013/001280, Report dated May 12, 2015, 6 pgs.
International Preliminary Report on Patentability for International Application No. PCT/AU2014/001049, Report dated May 17, 2016, 5 pgs.
International Preliminary Report on Patentability for International Application No. PCT/AU2014/050369, Report dated May 24, 2016, 8 pgs.
International Preliminary Report on Patentability for International Application No. PCT/AU2015/050135, Report dated Oct. 4, 2016, 13 pgs.
International Preliminary Report on Patentability for International Application No. PCT/AU2015/050215, Report dated Nov. 8, 2016, 4 pgs.
International Preliminary Report on Patentability for International Application No. PCT/AU2015/050422, Report dated Jan. 31, 2017, 8 pgs.
International Preliminary Report on Patentability for International Application No. PCT/AU2015/050724, Report dated May 23, 2017, 5 pgs.
International Preliminary Report on Patentability for International Application No. PCT/AU2015/050753, Report dated Jun. 13, 2017, 7 pgs.
International Preliminary Report on Patentability for International Application No. PCT/AU2015/050787, Report dated Jun. 13, 2017, 6 pgs.
International Preliminary Report on Patentability for International Application No. PCT/AU2016/050019, Report dated Jul. 25, 2017, 9 pgs.
International Preliminary Report on Patentability for International Application No. PCT/AU2016/050263, Report dated Oct. 10, 2017, 9 pgs.
International Search Report & Written Opinion for International Application No. PCT/AU2013/001280, Search Completed Jan. 16, 2014, dated Jan. 16, 2014, 8 Pgs.
International Search Report & Written Opinion for International Application PCT/AU2013/001279, Search Completed Jan. 9, 2014, dated Jan. 9, 2014, 9 Pgs.
International Search Report and Written Opinion for International Application No. PCT/AU2011/001127, date completed Nov. 11, 2011, dated Nov. 15, 2011, 13 pgs.
International Search Report and Written Opinion for International Application No. PCT/AU2012/001441, International Filing Date Nov. 23, 2012, Search Completed Feb. 26, 2013, dated Feb. 26, 2013, 14 pgs.
International Search Report and Written Opinion for International Application No. PCT/AU2014/001049, Search completed Feb. 10, 2015, dated Feb. 10, 2015, 8 Pgs.
International Search Report and Written Opinion for International Application No. PCT/AU2014/050369, Search completed Feb. 20, 2015, dated Feb. 20, 2015, 14 Pgs.
International Search Report and Written Opinion for International Application No. PCT/AU2015/050135, Search completed Jun. 30, 2015, dated Jun. 30, 2015, 26 Pgs.
International Search Report and Written Opinion for International Application No. PCT/AU2015/050422, Search completed Oct. 14, 2015, dated Oct. 14, 2015, 17 Pgs.
International Search Report and Written Opinion for International Application No. PCT/AU2015/050724, Search completed May 9, 2016, dated May 9, 2016, 8 Pgs.
International Search Report and Written Opinion for International Application No. PCT/AU2015/050753, Search completed Feb. 10, 2016, dated Feb. 10, 2016, 10 Pgs.
International Search Report and Written Opinion for International Application No. PCT/AU2015/050787, Search completed Mar. 16, 2016, dated Mar. 16, 2016, 10 Pgs.
International Search Report and Written Opinion for International Application No. PCT/AU2016/050019, Search completed May 4, 2016, dated May 4, 2016, 16 Pgs.
International Search Report and Written Opinion for International Application No. PCT/AU2016/050263, Search completed Nov. 16, 2016, dated Nov. 16, 2016, 8 Pgs.
International Search Report and Written Opinion for International Application No. PCT/AU2016/050430, Search completed Aug. 16, 2016, dated Aug. 16, 2016, 10 Pgs.
International Search Report and Written Opinion for International Application No. PCT/AU2016/050431, Search completed Aug. 16, 2016, dated Aug. 16, 2016, 11 Pgs.
International Search Report and Written Opinion for International Application No. PCT/AU2016/050439, Search completed Jul. 15, 2016, dated Jul. 15, 2016, 8 Pgs.
International Search Report and Written Opinion for International Application No. PCT/AU2017/050296, Search completed Jul. 28, 2017, dated Jul. 28, 2017, 10 Pgs.
International Search Report and Written Opinion for International Application No. PCT/AU2015/050215, Search completed Jul. 30, 2015, dated Jul. 30, 2015, 8 Pgs.
International Search Report for Australian Application 2011901829 Search Completed Feb. 6, 2012, dated Feb. 7, 2012, 3 pgs.
International Search Report for International Application No. PCT/AU2012/000511, International Filing Date May 11, 2012, Search Completed May 17, 2012, dated May 18, 2012, 4 pgs.
International Search Report for International Application No. PCT/AU2012/000512, International Filing Date May 11, 2012, Search Completed Jul. 10, 2012, dated Jul. 11, 2012, 4 pgs.
International Search Report for International Application No. PCT/AU2012/000513, International Filing Date May 11, 2012, Search Completed May 29, 2012, dated May 30, 2012, 5 pgs.
International Search Report for International Application No. PCT/AU2012/000515, International Filing Date May 11, 2012, Search Completed May 21, 2012, dated Jun. 4, 2012, 5 pgs.
International Search Report for International Application No. PCT/AU2012/000516, International Filing Date May 11, 2012, Search Completed Jul. 11, 2012, dated Jul. 12, 2012, 8 pgs.
International Search Report for International Application No. PCT/AU2012/000517, International Filing Date May 11, 2012, Search Completed Jun. 4, 2012, dated Jun. 6, 2012, 3 pgs.
International Search Report for International Application No. PCT/AU2012/000518, International Filing Date May 11, 2012, Search Completed Jun. 8, 2012, dated Jun. 12, 2012, 4 pgs.
International Type Search Report for International Application No. AU 2015902393, Search completed May 16, 2016, dated May 16, 2016, 8 Pgs.
Medtronic, Spinal Cord Stimulation, RestoreSensor Neurostimulator, Features and Specification: Specification, Printed Jun. 16, 2014, 2 pgs.
Medtronic, Spinal Cord Stimulation, RestoreSensor Neurostimulator, Features and Specification: Summary Printed Jun. 16, 2014, 1 pg.
Partial European Search Report for European Application No. 16775966.1, Search completed Oct. 26, 2018, dated Nov. 6, 2018, 11 Pgs.

(56) References Cited

OTHER PUBLICATIONS

Written Opinion for International Application No. PCT/AU2012/000511, International Filing Date May 11, 2012, Search Completed May 17, 2012, dated May 18, 2012, 5 pgs.
Written Opinion for International Application No. PCT/AU2012/000512, International Filing Date May 11, 2012, Search Completed Jul. 10, 2012, dated Jul. 11, 2012, 7 pgs.
Written Opinion for International Application No. PCT/AU2012/000513, International Filing Date May 11, 2012, Search Completed May 29, 2012, dated May 30, 2012, 10 pgs.
Written Opinion for International Application No. PCT/AU2012/000515, International Filing Date May 11, 2012, Search Completed May 21, 2012, dated Jun. 4, 2012, 4 pgs.
Written Opinion for International Application No. PCT/AU2012/000516, International Filing Date May 11, 2012, Search Completed Jul. 11, 2012, dated Jul. 12, 2012, 8 pgs.
Written Opinion for International Application No. PCT/AU2012/000517, International Filing Date May 11, 2012, Search Completed Jun. 4, 2012, dated Jun. 6, 2012, 5 pgs.
Written Opinion for International Application No. PCT/AU2012/000518, International Filing Date May 11, 2012, Search Completed Jun. 8, 2012, dated Jun. 12, 2012, 10 pgs.
Medtronic, RestoreSensor Neurostimulator, Retrieved from: http://web.archive.org/web/20150328092923/http://professional.medtronic.com:80/pt/neuro/scs/prod/restore-sensor/features-specifications/index.htm,, Capture Date Jul. 9, 2012, Printed on May 11, 2017.
"Advanced Pain Therapy using Neurostimulation for Chronic Pain", Medtronic RestoreSensor clinical trial paper,Clinical summary, Nov. 2011, pp. 32.
"Battelle Neurotechnology—Moving Beyond the Limits in Neurotechnology", Battelle, www.battelle.org, May 2014, pp. 1-2.
"Haptic technology", Wikipedia, Retrieved from: http://en.wikipedia.org/wiki/Haptic_technology, Last modified on Sep. 15, 2014, Printed on Sep. 15, 2014, 5 pgs.
"Implants for surgery, Cardiac pacemakers", IS-1 standard ISO 5841-3-2000, Oct. 15, 2000.
"Neural Bypass Technology Enables Movement in Paralyzed Patient", Posted on Jul. 29, 2014, 6 a.m. in Brain chips/computer interface, pp. 1-2.
"Spinal Cord Stimulation, About Spinal Cord Stimulation", Medtronic, Retrieved from: http://professional.medtronic.com/pt/neuro/scs/edu/about/index.htm, Printed on Jun. 16, 2014, 2 pgs.
"Wide bandwidth BioAmplifier", http://www.psylab.com/html/default_bioamp.htm, Printed Jan. 30, 2014, 1-3 pages.
Alam et al., "Evaluation of optimal electrode configurations for epidural spinal cord stimulation in cervical spinal cord injured rats", Journal of Neuroscience Methods, Mar. 2015, 28 pgs.
Al-Ani et al., "Automatic removal of high-amplitude stimulus artefact from neuronal signal recorded in the subthalamic nucleus", Journal of Neuroscience Methods, vol. 198, Issue 1, 2011, pp. 135-146.
Andreassen, S. et al., "Muscle Fibre Conduction Velocity in Motor Units of the Human Anterior Tibial Muscle: a New Size Principle Parameter", J. Physiol, (1987), 391, pp. 561-571.
Andy, "Parafascicular-Center Median Nuclei Stimulation for Intractable Pain and Dyskinesia (Painful-Dyskinesia)", Stereotactic and Functional Neurosurgery, Appl. Neurophysiol., 43, No. 3-5, 1980, pp. 133-144.
Balzer et al., "Localization of cervical and cervicomedullary stimulation leads for pain treatment using median nerve somatosensay evoked potential collision testing", Journal of Neurosurgery, Jan. 2011, vol. 114, No. 1: pp. 200-205.
Blum, A. R., "An Electronic System for Extracellular Neural Stimulation and Recording", Dissertation, Georgia Institute of Technology, Aug. 2007, Retrieved from http://smartech.gatech.edu/handle/1853/16192 on Jan. 30, 2012.
Borg et al., "Conduction velocity and refractory period of single motor nerve fibres in antecedent poliomyelitis", Journal of Neurology, Neurosurgery, and Psychiatry, vol. 50, 1987, 443-446.

Brown et al., "Impact of Deep Brain Stimulation on Upper Limb Askinesia in Parkinson's Disease", Annals of Neurology, 45, No. 4, 1999, pp. 473-488.
Budagavi et al., "Modelling of compound nerve action potentials health and disease", Engineering in Medicine and Biology Society, 1992 14th Annual International Conference of the IEEE. vol. 6. IEEE, 1992. pp 2600-2601.
Coquery et al., "Backward and forward masking in the perception of cutaneous stimuli", Perception & Psychophysics, 1973, vol. 13. No. 2, pp. 161-163.
Dawson, G. D., "The relative excitability and conduction velocity of sensory and motor nerve fibres in man", Journal of Physiology, 1956, vol. 131(2), pp. 436-451.
Devergnas A. et al., "Cortical potentials evoked by deep brain stimulation in the subthalamic area", Front Syst Neurosci. 2011; 5: 30. May 13, 2011. doi:10.3389/fnsys.2011.00030.
Dijkstra, E. A., "Ultrasonic Distance Detection for a Closed-Loop Spinal Cord Stimulation System", Proceedings—19th International Conference—IEEE/EMBS Oct. 30-Nov. 2, 1997, Chicago, IL., 4 pgs.
Dillier, N. et al., "Measurement of the electrically evoked compound action potential via a neural response telemetry system", Ann. Otol. Rhinol. Laryngol., vol. 111, No. 5, May 2002, pp. 407-414.
Doiron et al., "Persistent Na+ Current Modifies Burst Discharge by Regulating Conditional Backpropagation of Dendritic Spikes", Journal of Neurophysiology 89, No. 1 (Jan. 1, 2003): 324-337, doi:10.1152/jn.00729.2002.
England et al., "Increased Numbers of Sodium Channels Form Along Demyelinated Axons", Brain Research 548, No. 1-2 (May 10, 1991): 334-337.
Fagius, J. et al., "Sympathetic Reflex Latencies and Conduction Velocities in Normal Man", Journal of Neurological Sciences, 1980. vol. 47, pp. 433-448.
Falowski et al., "Spinal Cord Stimulation: an update", Neurotherapeutics: The Journal of the American Society for Experimental NeuroTherapeutics 5, No. 1, Jan. 2008, pp. 86-99.
Fisher, "F-Waves—Physiology and Clinical Uses", TheScientificWorldJournal, (2007) 7, pp. 144-160.
Franke, Felix et al., "An Online Spike Detection and Spike Classification Algorithm Capable of Instantaneous Resolution of Overlapping Spikes", Journal of Computational Neuroscience, 2010, vol. 29, No. 1-2, pp. 127-148.
French et al., "Information transmission at 500 bits/s by action potentials in a mechanosensory neuron of the cockroach", Neuroscience Letters, vol. 243, No. 1-3, Feb. 1, 1998, pp. 113-116.
Fuentes et al., "Spinal Cord Stimulation Restores Locomotion in Animal Models of Parkinson's Disease", Science, vol. 323, No. 5921, Mar. 20, 2009, pp. 1578-1582.
Gad et al., "Development of a multi-electrode array for spinal cord epidural stimulation to facilitate stepping and standing after a complete spinal cord injury in adult rats", Journal of NeuroEngineering and Rehabilitation 2013, 10:2, 18 pgs.
George et al., "Vagus nerve stimulation: a new tool for brain research and therapy", Biological Psychiatry 47, No. 4, Feb. 15, 2000, pp. 287-295.
Goodall, E. V., "Modeling Study of Activation and Propagation delays During Stimulation of Peripheral Nerve Fibres with a Tripolar Cuff Electrode", IEEE Transactions on Rehabilitation Engineering, vol. 3, No. 3, Sep. 1995, pp. 272-282.
Gorman et al., "ECAP Mapping of the Spinal Cord: Influence of Electrode Position on Aβ Recruitment", (2012).,In 16th Annual Meeting. Presented at the North American Neuromodulation Society, Las Vegas, NV.
Gorman et al., "Neural Recordings for Feedback Control of Spinal Cord Stimulation: Reduction of Paresthesia Variability.", 2013,In International Neuromodulation Society 11th World Congress. Presented at the International Neuromodulation Society 11th World Congress, Berlin, Germany.
Hallstrom et al., "Distribution of lumbar spinal evoked potentials and their correlation with stimulation-induced paresthesiae", (1991),Electroencephalography and clinical neurophysiology 80:126-139.

(56) References Cited

OTHER PUBLICATIONS

Harper, A. A. et al., "Conduction Velocity is Related to Morphological Cell Type in Rat Dorsal Root Ganglion Neurones", J. Physiol, (1985), 359, pp. 31-46.

He et al., "Perception threshold and electrode position for spinal cord stimulation", Pain, 59 (1994) 55-63 pages.

Herreras, "Local Field Potentials: Myths and Misunderstandings", Frontiers in Neural Circuits, Dec. 15, 2016, vol. 10, Article 1101, 16 pgs.

Holsheimer et al., "Optimum Electrode Geometry for Spinal Cord Stimulation: the Narrow Bipole and Tripole", Medical and Biological Engineering and Computing, 35, No. 5, 1997, pp. 493-497.

Holsheimer et al., "Significance of the Spinal Cord Position in Spinal Cord Stimulation", Acta Neurochir (1995) [Suppl] 64: 119-124 pages.

Holsheimer et al., "Spinal Geometry and Paresthesia Coverage in Spinal Cord Stimulation", (1998 paper) 8 Pages.

Huff, Terry B. et al., "Real-Time CARS Imaging Reveals a Calpain-Dependent Pathway for Paranodal Myelin Retraction during High-Frequency Stimulation", PLoS ONE vol. 6, issue 3 (Mar. 3, 2011): e17176, 11 pgs.

Kent et al., "Instrumentation to Record Evoked Potentials for Closed-Loop Control of Deep Brain Stimulation", Conf. Proc. IEEE Eng. Med Biol. Sol, Aug. 2012, 10 pgs.

Kent, AR. et al., "Recording evoked potentials during deep brain stimulation: development and validation of instrumentation to suppress the stimulus artefact", J Neural Eng. Jun. 2012; 9 (3):036004, Apr. 18, 2012. doi: 10.1088/1741-2560/9/3/036004.

Kim et al., "A Wavelet-Based Method for Action Potential Detection From Extracellular Neural Signal Recording With Low Signal-to-Noise Ratio", IEEE Transactions on Biomedical Engineering, vol. 50. No. 8, Aug. 2003.

Kim et al., "Cell Type-specific Changes of the Membrane Properties of Peripherally-axotomized Dorsal Root Ganglion Neurons in a Rat Model of Neuropathic Pain", Neuroscience 86, No. 1 (May 21, 1998): 301-309, doi:10.1016/S0306-4522(98)00022-0.

Krames et al., "Neuromodulation", 1st Edition, Academic Press, 2009, p. 540-541.

Krarup, Christian, "Compound sensory action potential in normal and pathological human nerves", Muscle & nerve, vol. 29, No. 4 (2004), pp. 465-483.

Krishnan et al., "Excitability Differences in Lower-Limb Motor Axons During and After Ischemia", Muscle & nerve, vol. 31, No. 2 (2005), pp. 205-213.

Kumar et al., "Deep Brain Stimulation for Intractable Pain: a 15-year Experience", Neurosurgery, Issue 40, No. 4, Apr. 1997, pp. 736-747.

Kumar et al., "Double-blind evaluation of subthalamic nucleus deep brain stimulation in advanced Parkinson's disease", by the American Academy of Neurology, 51, No. 3, Sep. 1, 1998, pp. 850-855.

Kumar et al., "Globus Pallidus Deep Brain Stimulation for Generalized Dystonia: Clinical and PET Investigation", Neurology, 53, No. 4, 1999, pp. 871-874.

Laird et al., "A Model of Evoked Potentials in Spinal Cord Stimulation", IEEE Engineering in Medicine & Biology Society, 35th Annual Conference. Osaka, Japan: Jul. 3-7, 2013, pp. 6555-6558.

Lempka, Scott, "The Electrode-Tissue Interface During Recording and Stimulation in the Central Nervous System", published on May 2010.

Levy et al., "Incidence and Avoidance of Neurologic Complications with Paddle Type Spinal Cord Stimulation Leads", Neuromodulation 14(15), Sep. 2011, pp. 412-422.

Li, S. et al., "Resonant antidromic cortical circuit activation as a consequence of high-frequency subthalamic deep-brain stimulation", J Neurophysiol. Dec. 2007; 98(6): 3525-37. First published Oct. 10, 2007. doi:10.1152/jn.00808.2007.

Ma et al., "Similar Electrophysiological Changes in Axotomized and Neighboring Intact Dorsal Root Ganglion Neurons", Journal of Neurophysiology 89, No. 3 (Mar. 1, 2003): 1588-1602, doi:10.1152/jn.00855.2002.

Macefield, "Spontaneous and Evoked Ectopic Discharges Recorded from Single Human Axons", Muscle & Nerve 21, No. 4, Apr. 1998, pp. 461-468.

Mahnam et al., "Measurement of the current-distance relationship using a novel refractory interaction technique", J. Neural Eng. 6(2): 036005, published May 20, 2009, 22 pgs.

Markandey, Vishal, "ECG Implementation on the TMS320C5515 DSP Medical Development Kit (MDK)", Texas Instruments Application Report Jun. 2010, 35 pgs.

Massachusetts Institute of Techn, "The Compound Action Potential of the Frog Sciatic Nerve", Quantitative Physiology: Cells and Tissues. Fall, 1999, Retrieved from http://umech.mit.edu/freeman/6.021J/2001/lab.pdf on May 22, 2012.

Matzner et al., "Na+ Conductance and the Threshold for Repetitive Neuronal Firing", Brain Research 597, No. 1 (Nov. 27, 1992): 92-98, doi:10.1016/0006-8993(92)91509-D.

Mcgill, Kevin et al., "On the Nature and Elimination of Stimulus Artifact in Nerve Signals Evoked and Recorded Using Surface Electrodes", IEEE Transactions on Biomedical Engineering, vol. BME-29, No. 2, Feb. 1982, pp. 129-137.

Melzack et al., "Pain mechanisms: a new theory", Science, New York, New York, vol. 150, No. 3699, Nov. 19, 1965, pp. 971-979.

Miles et al., "An Electrode for Prolonged Stimulation of the Brain", Proc. 8th Meeting World Soc. Stereotactic and Functional Neurosurgery, Part III, Zurich, 1981, Appl. Neurophysiol, 45, 1982, pp. 449-445.

Misawa et al., "Neuropathic Pain Is Associated with Increased Nodal Persistent Na(+) Currents in Human Diabetic Neuropathy", Journal of the Peripheral Nervous System: JPNS, 14, No. 4 (Dec. 2009): 279-284.

Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi:10.1016/0304-3959(84)90013-7.

Oakley et al., "Spinal Cord Stimulation: Mechanisms of Action", Spine 27, No. 22, Nov. 15, 2002, pp. 2574-2583.

Oakley et al., "Transverse Tripolar Spinal Cord Stimulation: Results of an International Multicenter Study", Neuromodulation, vol. 9, No. 3, 2006, pp. 192-203.

Obradovic et al., "Effect of pressure on the spinal cord during spinal cord stimulation in an animal model", Poster, 18th Annual Meeting of the North American Neuromodulation Society, Dec. 11-14, 2014, Las Vegas.

Oh et al., "Long-term hardware-related complications of deep brain stimulation", Neurosurgery, vol. 50, No. 6, Jun. 2002, pp. 1268-1274, discussion pp. 1274-1276.

Olin et al., "Postural Changes in Spinal Cord Stimulation Perceptual Thresholds", Neuromodulation, vol. 1, No. 4, 1998, pp. 171-175.

Opsommer, E. et al., "Determination of Nerve Conduction Velocity of C-fibres in Humans from Thermal Thresholds to Contact Heat (Thermode) and from Evoked Brain Potentials to Radiant Heat (CO2 Laser)", Neurophysiologie Clinique 1999, vol. 29, pp. 411-422.

Orstavik, Kristin et al., "Pathological C-fibres in patients with a chronic painful condition", Brain (2003), 126, 567-578.

Ouyang et al., "Compression Induces Acute Demyelination and Potassium Channel Exposure in Spinal Cord", Journal of Neurotrauma 27, No. 6, Jun. 2010, 1109-1120, doi:10.1089/neu.2010.1271.

Parker et al., "Closing the Loop in Neuromodulation Therapies: Spinal Cord Evoked Compound Action Potentials During Stimulation for Pain Management (230).", 2011, In 15th Annual Meeting, North American Neuromodulation Society (p. 48). Presented at the North American Neuromodulation Society, Las Vegas.

Parker et al., "Compound action potentials recorded in the human spinal cord during neurostimulation for pain relief", Pain, 2012, vol. 153, pp. 593-601.

Parker et al., "Electrically Evoked Compound Action Potentials Recorded From the Sheep Spinal Cord", Neuromodulation, vol. 16, 2013, pp. 295-303.

Penar et al., "Cortical Evoked Potentials Used for Placement of a Laminotomy Lead Array: A Case Report", Neuromodulation: Technology at the Neural Interface, accessed Apr. 19, 2011, doi:10.1111/j.1525-1403.2011.00352.x.

(56) References Cited

OTHER PUBLICATIONS

Rattay, "Analysis of Models for External Stimulation of Axons", IEEE Transactions on Biomedical Engineering, vol. BME-33, No. 10, Oct. 1986, pp. 974-977.
Richter et al., "EMG and SSEP Monitoring During Cervical Spinal Cord Stimulation", Journal of Neurosurgical Review 2011, Southern Academic Press, 1(S1), 2011, pp. 61-63.
Ridder et al., "Burst Spinal Cord Stimulation for Limb and Back Pain", World Neurosurgery, 2013, 9 pgs.
Ross et al., "Improving Patient Experience with Spinal Cord Stimulation Implications of Position-Related Changes in Neurostimulation", Neuromodulation 2011; e-pub ahead of print. DOI: 10.1111/j.1525-1403.2011.00407.x 6 pages.
Roy, S. H. et al., "Effects of Electrode Location on Myoelectric Conduction Velocity and Median Frequency Estimates", J. Appl. Physiol. 61 (4), 1986, pp. 1510-1517.
Sayenko et al., "Neuromodulation of evoked muscle potentials induced by epidural spinal-cord stimulation in paralyzed individuals", Journal of Neurophysiology, vol. 111, No. 5, 2014, pp. 1088-1099, First published Dec. 11, 2013.
Schmidt et al., "Gating of tactile input from the hand", Exp Brain Res, 1990, 79, pp. 97-102.
Siegfried et al., "Bilateral Chronic Electrostimulation of Ventroposterolateral Pallidum: A New Therapeutic Approach for Alleviating all Parkinsonian Symptoms", Neurosurgery, 35, No. 6, Dec. 1994, pp. 1126-1130.
Siegfried et al., "Intracerebral Electrode Implantation System", Journal of Neurosurgery, vol. 59, No. 2, Aug. 1983, pp. 356-3591.
Srinivasan, S., "Electrode/Electrolyte Interfaces: Structure and Kinetics of Charge Transfer", Fuel Cells, 2006, Chapter 2, 67 Pages.
Struijk, "The Extracellular Potential of a Myelinated Nerve Fiber in an Unbounded Medium and in Nerve Cuff Models", Biophysical Journal vol. 72 Jun. 1997 2457-2469.
Struijk et al., "Paresthesia Thresholds in Spinal Cord Stimulation: A Comparison of Theoretical Results with Clinical Data", IEEE Transactions on Rehabilitation Engineering, vol. 1, No. 2, Jun. 1993, pp. 101-108.
Struijk et al., "Excitation of Dorsal Root Fibers in Spinal Cord Stimulation: a Theoretical Study", IEEE Transactions on Biomedical Engineering, Jul. 1993, vol. 40, No. 7, pp. 632-639.
Sufka et al., "Gate Control Theory Reconsidered", Brain and Mind, 3, No. 2, 2002, pp. 277-290.
Tamura et al., "Increased Nodal Persistent Na+ Currents in Human Neuropathy and Motor Neuron Disease Estimated by Latent Addition", Clinical Neurophysiology 117, No. 11 (Nov. 2006): 2451-2458, doi:10.1016/j.clinph.2006.07.309.
Tasker, "Deep Brain Stimulation is Preferable to Thalamotomy for Tremor Suppression", Surgical Neurology, 49, No. 2, 1998, pp. 145-153.
Taylor et al., "Spinal Cord Stimulation for Chronic Back and Leg Pain and Failed Back Surgery Syndrome: A Systematic Review and Analysis of Prognostic Factors", SPINE, vol. 30, No. 1, 2004, pp. 152-160.
Texas Instruments, "Precision, Low Power Instrumentation Amplifiers", Texas Instruments SBOS051B Oct. 1995, Revised Feb. 2005, 20 pgs.
Tomas et al., "Dorsal Root Entry Zone (DREZ) Localization Using Direct Spinal Cord Stimulation Can Improve Results of the DREZ Thermocoagulation Procedure for Intractable Pain Relief", Pain, 2005, vol. 116, pp. 159-163.
Tronnier et al., "Magnetic Resonance Imaging with Implanted Neurostimulators: An In Vitro and In Vivo Study", Jan. 1999, Neurosurgery, vol. 44(1), p. 118-125 (Year: 1999).
Tscherter et al., "Spatiotemporal Characterization of Rhythmic Activity in Rat Spinal Cord Slice Cultures", European Journal of Neuroscience 14, No. 2 (2001), pp. 179-190.
Van Den Berg et al., "Nerve fiber size-related block of action currents by phenytoin in mammalian nerve", Epilepsia, Nov. 1994, 35(6), pp. 1279-1288.
Villavicencio, Alan T., "Laminectomy versus Percutaneous Electrode Placement for Spinal Cord Stimulation," Neurosurgery, vol. 46 (2), Feb. 2000, pp. 399-405.
Vleggeert, Lankamp et al., "Electrophysiology and morphometry of the Aalpha- and Abeta-fiber populations in the normal and regenerating rat sciatic nerve", Experimental Neurology, vol. 187, No. 2, Jun. 1, 2004, Available online Apr. 2, 2004, pp. 337-349.
Woessner, "Blocking Out the Pain, Electric Nerve Block Treatments for Sciatic Neuritis", Retrieved from: http://www.practicalpainmanagement.com/pain/spine/radiculopathy/blocking-out-pain, Last updated Jan. 10, 2012.
Wolter et al., "Effects of sub-perception threshold spinal cord stimulation in neuropathic pain: A randomized controlled double-blind crossover study", European Federation of International Association for the Study of Pain Chapters, 2012, pp. 648-655.
Wu et al., "Changes in Aβ Non-nociceptive Primary Sensory Neurons in a Rat Model of Osteoarthritis Pain", Molecular Pain 6, No. 1 (Jul. 1, 2010): 37, doi:10.1186/1744-8069-6-37.
Xie et al., "Functional Changes in Dorsal Root Ganglion Cells after Chronic Nerve Constriction in the Rat", Journal of Neurophysiology 73, No. 5 (May 1, 1995): 1811-1820.
Xie et al., "Sinusoidal Time-Frequency Wavelet Family and its Application in Electrograstrographic Signal Analysis", Proceedings of the 20th Annual International Conference of the IEEE Engineering in Medicine and Biology Society, vol. 20, No. 3, Oct. 29, 1998, pp. 1450-1453.
Yamada et al., "Extraction and Analysis of the Single Motor Unit F-Wave of the Median Nerve", EMG Methods for Evaluating Muscle and Nerve Function, InTech, 2012, 15 pgs.
Yearwood, T. L., "Pulse Width Programming in Spinal Cord Stimulation: a Clinical Study", Pain Physician. 2010. Vol. 13, pp. 321-335.
Yingling et al., "Use of Antidromic Evoked Potentials in Placement of Dorsal Cord Disc Electrodes", Applied Neurophysiology, 1986, vol. 49, pp. 36-41.
Yuan, S. et al., "Recording monophasic action potentials using a platinum-electrode ablation catheter", Europace. Oct. 2000; 2(4):312-319.
Australian Examination Report for Application No. 2019283936, dated Apr. 1, 2021, 7 pages.
International Search Report for International Application No. PCT/AU2019/051151, International Filing Date Oct. 22, 2019, Search Completed Feb. 24, 2020, dated Feb. 24, 2020, 9 pgs.
International Search Report for International Application No. PCT/AU2019/051160, International Filing Date Oct. 23, 2019, Search Completed Jan. 28, 2020, dated Jan. 28, 2020, 13 pgs.
International Search Report for International Application No. PCT/AU2019/051163, International Filing Date Oct. 23, 2019, Search Completed Jan. 21, 2020, dated Jan. 31, 2020, 8 pgs.
International Search Report for International Application No. PCT/AU2019/051197, International Filing Date Oct. 30, 2019, Search Completed Jan. 21, 2020, dated Jan. 21, 2020, 15 pgs.
International Search Report for International Application No. PCT/AU2019/051210, International Filing Date Nov. 2, 2019, Search Completed Feb. 4, 2020, dated Feb. 4, 2020, 10 pgs.
Japanese Office Action for Application No. 2018-552138, dated Mar. 1, 2021, 7 pages with English translation.
"Evoke 12C Percutaneous Leads", Saluda Medical, specifications available in the "Evoke Surgical Guide", version 6, http://www.saludamedical.com/manuals/, retrieved May 2017.
Bratta et al., "Orderly Stimulation of Skeletal Muscle Motor Units with Tripolar Nerve Cuff Electrode", IEEE Transactions on Biomedical Engineering, vol. 36, No. 8, 1989.
Celestin et al., "Pretreatment Psychosocial Variables as Predictors of Outcomes Following Lumbar Surgery and Spinal Cord Stimulation: A Systematic Review and Literature Synthesis", American Academy of Pain Medicine, 2009, vol. 10, No. 4, pp. 639-653. doi:10.1111/j.1526-4637.2009.00632.X.
Cong et al., "A 32-channel modular bi-directional neural interface system with embedded DSP for closed-loop operation", 40th European Solid State Circuits Conference (ESSCIRC), 2014, pp. 99-102.

(56) References Cited

OTHER PUBLICATIONS

Connolly et al., "Towards a platform for prototyping control systems for optimization of neuromodulation therapies", IEEE Biomedical Circuits and Systems Conference (BioCAS), 2015, pp. 1-4.
Delgado et al., "Measurement and interpretation of electrokinetic phenomena", Pure Appl. Chem., 2005, vol. 77, No. 10, pp. 1753-1805.
Fitzpatrick et al., "A Nerve Cuff Design for the Selective Activation and Blocking of Myelinated Nerve Fibers", IEEE Engineering in Medicine and Biology Society, vol. 13, No. 2, 1991.
Howell et al., "Evaluation of Intradural Stimulation Efficiency and Selectivity in a Computational Model of Spinal Cord Stimulation", PLOS ONE, DOI:10.1371/journal.pone.0114938, Dec. 23, 2014.
Jones et al., "Scaling of Electrode- Electrolyte Interface Model Parameters In Phosphate Buffered Saline", IEEE Transactions on Biomedical Circuits and Systems, 2015, vol. 9, No. 3, pp. 441-448.
North et al., "Prognostic value of psychological testing in patients undergoing spinal cord stimulation: a prospective study", Neurosurgery, Aug. 1, 1996, vol. 39, Issue 2, pp. 301-311. https://doi.org/10.1097/00006123-199608000-00013.
Peterson et al., "Stimulation artifact rejection in closed-loop, distributed neural interfaces", ESSCIRC, 42nd European Solid-State Circuits Conference, Lausanne, 2016, pp. 233-235.
Rijkhoff et al., "Acute Animal Studies on the Use of Anodal Block to Reduce Urethral Resistance in Sacral Root Stimulation", IEEE Transactions on Rehabilitation Engineering, vol. 2, No. 2, 1994.
Rijkhoff et al., "Orderly Recruitment of Motoneurons in an Acute Rabbit Model", Annual International Conference of the IEEE Engineering in Medicine and Biology Society, vol. 20, No. 5, 1998.
Scott et al., "Compact Nonlinear Model of an Implantable Electrode Array for Spinal Cord Stimulation (SCS)", IEEE Transactions on Biomedical Circuits and Systems, 2014, vol. 8, No. 3, pp. 382-390.
Stanslaski et al., "Design and Validation of a Fully Implantable, Chronic, Closed-Loop Neuromodulation Device With Concurrent Sensing and Stimulation", IEEE Transactions on Neural Systems and Rehabilitation Engineering, Jul. 2012, Date of Publication: Jan. 23, 2012, vol. 20, No. 4, pp. 410-421, DOI: 10.1109/TNSRE.2012.2183617.
Zhou et al., "A High Input Impedance Low Noise Integrated Front-End Amplifier for Neural Monitoring", IEEE Transactions on Biomedical Circuits and Systems, 2016, vol. 10, No. 6, pp. 1079-1086.
Extended European Search Report for European Application No. 17778477.4, report completed Nov. 12, 2019, dated Nov. 20, 2019, 7 pgs.
Extended European Search Report for European Application No. 17814341.8, report completed Dec. 12, 2019, report dated Jan. 2, 2020, 8 pgs.
Japanese Office Action for Application No. 2017-546830, dated Feb. 20, 2020, 5 pages with English translation.
Extended European Search Report in European Appln No. 18910394.8, dated Oct. 15, 2021, 8 pages.
"Percutaneous Lead Kit", St. Jude Medical Clinician's Manual, Models 3143, 3146, 3149, 3153, 3156, 3159, 3183, 3186, 3189, published Sep. 2016, 24 pages.

\* cited by examiner

Segmented sense electrode

METHOD AND APPARATUS FOR MEASUREMENT OF NEURAL RESPONSE

CROSS-REFERENCE TO RELATED APPLICATIONS

This application is a continuation of U.S. application Ser. No. 15/184,787, filed Jun. 16, 2016, which is a continuation of U.S. application Ser. No. 14/117,144, filed Nov. 12, 2013 and issued as U.S. Pat. No. 9,386,934 on Jul. 12, 2016, which application is a national stage of Application No. PCT/AU2012/000511, filed May 11, 2012, which application claims the benefit of Australian Provisional Patent Application No. 2011901817, filed May 13, 2011, the disclosures of which are incorporated herein by reference.

TECHNICAL FIELD

The present invention relates to measurement of a neural response to a stimulus, and in particular relates to measurement of a compound action potential by using one or more electrodes implanted proximal to the neural pathway.

BACKGROUND OF THE INVENTION

Neuromodulation is used to treat a variety of disorders including chronic pain, Parkinson's disease, and migraine. A neuromodulation system applies an electrical pulse to tissue in order to generate a therapeutic effect. When used to relieve chronic pain, the electrical pulse is applied to the dorsal column (DC) of the spinal cord or dorsal root ganglion (DRG). Such a system typically comprises an implanted electrical pulse generator, and a power source such as a battery that may be rechargeable by transcutaneous inductive transfer. An electrode array is connected to the pulse generator, and is positioned in the dorsal epidural space above the dorsal column. An electrical pulse applied to the dorsal column by an electrode causes the depolarisation of neurons, and generation of propagating action potentials. The fibres being stimulated in this way inhibit the transmission of pain from that segment in the spinal cord to the brain.

While the clinical effect of spinal cord stimulation (SCS) is well established, the precise mechanisms involved are poorly understood. The DC is the target of the electrical stimulation, as it contains the afferent Aβ fibres of interest. Aβ fibres mediate sensations of touch, vibration and pressure from the skin. The prevailing view is that SCS stimulates only a small number of Aβ fibres in the DC. The pain relief mechanisms of SCS are thought to include evoked antidromic activity of Aβ fibres having an inhibitory effect, and evoked orthodromic activity of Aβ fibres playing a role in pain suppression. It is also thought that SCS recruits Aβ nerve fibres primarily in the DC, with antidromic propagation of the evoked response from the DC into the dorsal horn thought to synapse to wide dynamic range neurons in an inhibitory manner.

Neuromodulation may also be used to stimulate efferent fibres, for example to induce motor functions. In general, the electrical stimulus generated in a neuromodulation system triggers a neural action potential which then has either an inhibitory or excitatory effect. Inhibitory effects can be used to modulate an undesired process such as the transmission of pain, or to cause a desired effect such as the contraction of a muscle.

The action potentials generated among a large number of fibres sum to form a compound action potential (CAP). The CAP is the sum of responses from a large number of single fibre action potentials. The CAP recorded is the result of a large number of different fibres depolarising. The propagation velocity is determined largely by the fibre diameter and for large myelinated fibres as found in the dorsal root entry zone (DREZ) and nearby dorsal column the velocity can be over 60 ms$^{-1}$. The CAP generated from the firing of a group of similar fibres is measured as a positive peak potential P1, then a negative peak N1, followed by a second positive peak P2. This is caused by the region of activation passing the recording electrode as the action potentials propagate along the individual fibres.

To better understand the effects of neuromodulation and/or other neural stimuli, it is desirable to record a CAP resulting from the stimulus. However, this can be a difficult task as an observed CAP signal will typically have a maximum amplitude in the range of microvolts, whereas a stimulus applied to evoke the CAP is typically several volts. Electrode artefact usually results from the stimulus, and manifests as a decaying output of several millivolts throughout the time that the CAP occurs, presenting a significant obstacle to isolating the CAP of interest. Some neuromodulators use monophasic pulses and have capacitors to ensure there is no DC flow to the tissue. In such a design, current flows through the electrodes at all times, either stimulation current or equilibration current, hindering spinal cord potential (SCP) measurement attempts. Moreover, high-pass filter poles in measurement circuitry generate increased electrical artefact with mono-phasic pulses. The capacitor recovers charge at the highest rate immediately after the stimulus, undesirably causing greatest artefact at the same time that the evoked response occurs.

To resolve a 10 uV SCP with 1 uV resolution in the presence of an input 5V stimulus, for example, requires an amplifier with a dynamic range of 134 dB, which is impractical in implant systems. As the neural response can be contemporaneous with the stimulus and/or the stimulus artefact, CAP measurements present a difficult challenge of amplifier design. In practice, many non-ideal aspects of a circuit lead to artefact, and as these mostly have a decaying exponential appearance that can be of positive or negative polarity, their identification and elimination can be laborious.

A number of approaches have been proposed for recording a CAP. King (U.S. Pat. No. 5,913,882) measures the spinal cord potential (SCP) using electrodes which are physically spaced apart from the stimulus site. To avoid amplifier saturation during the stimulus artefact period, recording starts at least 1-2.5 ms after the stimulus. At typical neural conduction velocities, this requires that the measurement electrodes be spaced around 10 cm or more away from the stimulus site, which is undesirable as the measurement then necessarily occurs in a different spinal segment and may be of reduced amplitude.

Nygard (U.S. Pat. No. 5,758,651) measures the evoked CAP upon an auditory nerve in the cochlea, and aims to deal with artefacts by a sequence which comprises: (1) equilibrating electrodes by short circuiting stimulus electrodes and a sense electrode to each other; (2) applying a stimulus via the stimulus electrodes, with the sense electrode being open circuited from both the stimulus electrodes and from the measurement circuitry; (3) a delay, in which the stimulus electrodes are switched to open circuit and the sense electrode remains open circuited; and (4) measuring, by switching the sense electrode into the measurement circuitry. Nygard also teaches a method of nulling the amplifier following the stimulus. This sets a bias point for the amplifier during the period following stimulus, when the electrode is not in equilibrium. As the bias point is reset each cycle, it is susceptible to noise. The Nygard measurement amplifier is a differentiator during the nulling phase which makes it susceptible to pickup from noise and input transients when a non-ideal amplifier with finite gain and bandwidth is used for implementation.

Daly (US Patent Application No. 2007/0225767) utilizes a biphasic stimulus plus a third phase "compensatory" stimulus which is refined via feedback to counter stimulus artefact. As for Nygard, Daly's focus is the cochlea. Daly's measurement sequence comprises (1) a quiescent phase where stimulus and sense electrodes are switched to $V_{dd}$; (2) applying the stimulus and then the compensatory phase, while the sense electrodes are open circuited from both the stimulus electrodes and from the measurement circuitry; (3) a load settling phase of about 1 µs in which the stimulus electrodes and sense electrodes are shorted to $V_{dd}$; and (4) measurement, with stimulus electrodes open circuited from $V_{dd}$ and from the current source, and with sense electrodes switched to the measurement circuitry. However a 1 µs load settling period is too short for equilibration of electrodes which typically have a time constant of around 100 µs. Further, connecting the sense electrodes to $V_{dd}$ pushes a charge onto the sense electrodes, exacerbating the very problem the circuit is designed to address.

Evoked responses are less difficult to detect when they appear later in time than the artifact, or when the signal-to-noise ratio is sufficiently high. The artifact is often restricted to a time of 1-2 ms after the stimulus and so, provided the neural response is detected after this time window, data can be obtained. This is the case in surgical monitoring where there are large distances between the stimulating and recording electrodes so that the propagation time from the stimulus site to the recording electrodes exceeds 2 ms. Because of the unique anatomy and tighter coupling in the cochlea, cochlear implants use small stimulation currents relative to the tens of mA sometimes required for SCS, and thus measured signals in cochlear systems present a relatively lower artifact. However to characterize the responses from the dorsal columns, high stimulation currents and close proximity between electrodes are required, and therefore the measurement process must overcome artifact directly, in contrast to existing "surgical monitoring" techniques.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect the present invention provides a method for measuring a neural response to a stimulus, the method comprising:

settling measurement circuitry prior to a stimulus, by connecting a sense electrode to the measurement circuitry to allow the measurement circuitry to settle towards a bioelectrically defined steady state;

recovering charge on stimulus electrodes by short circuiting the stimulus electrodes to each other;

applying an electrical stimulus from the stimulus electrodes to neural tissue, while keeping the sense electrode disconnected from the measurement circuitry;

imposing a delay during which the stimulus electrodes are open circuited and the sense electrode is disconnected from the measurement circuitry and from the stimulus electrodes; and after the delay, measuring a neural response signal present at the sense electrode by connecting the sense electrode to the measurement circuitry.

According to a second aspect the present invention provides an implantable device for measuring a neural response to a stimulus, the device comprising:

a plurality of electrodes including one or more nominal stimulus electrodes and one or more nominal sense electrodes;

a stimulus source for providing a stimulus to be delivered from the one or more stimulus electrodes to neural tissue;

measurement circuitry for amplifying a neural signal sensed at the one or more sense electrodes; and a control unit configured to control application of a stimulus to the neural tissue and measurement of an evoked neural response, the control unit configured to settle the measurement circuitry prior to a stimulus by connecting the or each sense electrode to the measurement circuitry to allow the measurement circuitry to settle towards a bioelectrically defined steady state, the control unit further configured to recover charge on the stimulus electrodes by short circuiting the stimulus electrodes to each other, the control unit further configured to cause the stimulus source to apply an electrical stimulus from the stimulus electrodes to neural tissue while keeping the or each sense electrode disconnected from the measurement circuitry, the control unit further configured to impose a delay during which the stimulus electrodes are open circuited and the sense electrode is disconnected from the measurement circuitry and from the stimulus electrodes, and the control unit further configured to measure a neural response signal present at the sense electrode by connecting the or each sense electrode to the measurement circuitry after the delay.

It is to be understood herein that open circuiting of an electrode involves ensuring that the electrode is disconnected from other electrodes, the stimulus source, the measurement circuitry and from voltage rails. Ensuring that the sense electrode is disconnected from the stimulus electrodes during the delay period avoids charge transfer onto the sense electrode(s) and associated artefact. The present invention recognizes that connecting the sense electrodes to the stimulus electrodes during a post-stimulus delay period can undesirably give rise to such charge transfer and associated artefact, particularly if the delay is short relative to the time constant of the stimulus electrodes, the latter typically being around 100 µs. The sense electrode is preferably open circuited during the post-stimulus delay so as to be disconnected from all other electrodes of the array, to prevent such charge transfer to the sense electrode from other non-stimulus electrodes. With particular regard to the case of spinal cord response measurement, the present invention recognizes that in the spinal cord, the stimulation electrodes may never reach equilibrium at the stimulation rates used for chronic pain, so that connecting them to the stimulating electrodes at any time would increase artefact. This lack of equilibrium is due to the nature of the Helmholtz layer which causes fractional pole variation in the electrode impedance with frequency, with time constants as long as tens of milliseconds.

The present invention recognizes that it is beneficial to provide for pre-stimulus settling of the measurement circuitry towards a bio-electrically defined steady state. This ensures that charge recovery occurs in the settling stage prior to the stimulus and not during or immediately after the stimulus and thus does not give rise to artefact during or immediately after the stimulus. Thus, the present invention captures the bio-electrically defined steady state as reference point voltage at the end of the measurement cycle, when the system is in its most stable state. The system then amplifies the difference between the captured voltage and the reference point voltage. Where repeated measurement cycles are undertaken, the present invention further permits the measurement amplifier to accumulate a bias point over multiple cycles rather than re-setting the bias point each cycle. The settle period is preferably sufficiently long to permit the electrodes and circuitry to reach an equilibrium, and for example the settle period may be around 1 ms or greater, as permitted by a stimulus rate. For example if therapeutic stimuli are applied to a dorsal column at about 100 Hz and do not give rise to a slow neural response, then after the approximately 2 ms duration of an evoked fast response up to about 8 ms would be available for the settling period. However, this is generally longer than required and the settling period may be substantially less than 8 ms.

The delay may be in the range of substantially zero to 1 ms, and for example may be about 0.3 ms. Such embodiments permit onset of the neural response to be observed, this typically occurring about 0.3 ms after the stimulus for an electrode 3 cm away from the stimulus site. In embodiments in which an amplifier of the measurement circuitry has a very high dynamic range, and/or if using a measurement electrode closer to the stimulus electrode, the delay may be set to a smaller value for example in the range of 50-200 μs. The delay is preferably set to a value which ensures the measurement amplifier is not saturated and therefore performs linearly at all times when connected without experiencing clipping, and for example a feedback loop may be implemented to determine a suitable delay which avoids amplifier saturation for a given stimulus.

In preferred embodiments of the invention, the signal from the or each sense electrode is passed to a sample-and-hold circuit at the input of a measurement amplifier. In such embodiments measurements of a single evoked response may be obtained from a plurality of sense electrodes, even if the measurement circuitry of each electrode is connected to the control unit only by a two wire bus or the like, as is commonly required in implanted electrode arrays.

Additionally or alternatively, a buffer or follower amplifier is preferably provided in some embodiments, between the sense electrode and the measurement amplifier. The buffer is preferably connected to the sense electrode without interposed switches, so that the high reverse impedance of the buffer effectively prevents switching transients from being conveyed to the sense electrode, thereby avoiding artefact which may arise upon the sense electrode if subjected to such transients. The buffer amplifier is also preferably configured to give current gain to drive a storage capacitor of a sample and hold circuit. A series capacitor may be interposed between the sense electrode and the buffer to avoid DC transfer with the tissue in the event where the amplifier malfunctions. This capacitor also allows the bias voltage of the amplifier to equilibrate as the electrode voltage can drift over time periods of several tens of seconds.

In preferred embodiments of the invention, the stimulus and sense electrodes are selected from an implanted electrode array. The electrode array may for example comprise a linear array of electrodes arranged in a single column along the array. Alternatively the electrode array may comprise a two dimensional array having two or more columns of electrodes arranged along the array. Preferably, each electrode of the electrode array is provided with an associated measurement amplifier, to avoid the need to switch the sense electrode(s) to a shared measurement amplifier, as such switching can add to measurement artefact. Providing a dedicated measurement amplifier for each sense electrode is further advantageous in permitting recordings to be obtained from multiple sense electrodes simultaneously.

The measurement may be a single-ended measurement obtained by passing a signal from a single sense electrode to a single-ended amplifier. Alternatively, the measurement may be a differential measurement obtained by passing signals from two sense electrodes to a differential amplifier.

While recovering charge by short circuiting the stimulus electrodes together, it may in some embodiments be advantageous to disconnect the sense electrode from the measurement circuitry, for example by setting a sample-and-hold circuit to "hold".

Embodiments of the invention may prove beneficial in obtaining a CAP measurement which has lower dynamic range and simpler morphology as compared to systems more susceptible to artefact. Such embodiments of the present invention may thus reduce the dynamic range requirements of implanted amplifiers, and may avoid or reduce the complexity of signal processing systems for feature extraction, simplifying and miniaturizing an implanted integrated circuit. Such embodiments may thus be particularly applicable for an automated implanted evoked response feedback system for stimulus control. Thus, in a further aspect, the present invention provides a method for feedback control of a neural stimulus, the method comprising an implanted control unit obtaining a CAP measurement in accordance with the method of the first aspect, and the implanted control unit using the obtained CAP measurement to control the delivery of subsequent neural stimuli by the implant.

In some embodiments of the invention, an averaged CAP measurement may be obtained by (i) delivering a first biphasic stimulus which starts with a pulse of a first polarity and then delivers a pulse of a second polarity opposite to the first polarity, and obtaining a first measurement of a CAP evoked by the first stimulus; (ii) delivering a second biphasic stimulus which starts with a pulse of the second polarity and then delivers a pulse of the first polarity, and obtaining a second measurement of a CAP evoked by the second stimulus; and (iii) taking an average of the first measurement and the second measurement to obtain an averaged measurement. Such embodiments exploit the observation that artefact polarity usually reflects the stimulus polarity, whereas the CAP polarity is independent of the stimulus polarity and is instead determined by the anatomy and physiology of the spinal cord membrane, so that averaging the first and second measurements will tend to selectively cancel out artefact. Further noting that for some electrode polarity configurations, such as monopolar, an "anodic first" biphasic stimulus usually has a lower stimulus threshold for neural recruitment than a "cathodic first" biphasic stimulus, the averaged measurement may have a morphology of either (i) a typical CAP of half amplitude if only the anodic-first stimulus exceeds the stimulus threshold; (ii) the average of two CAPs of different amplitude if both stimuli exceed the stimulus threshold but the cathodic first stimulus does not cause saturation recruitment; or (iii) a typical CAP if both stimuli exceed saturation recruitment. Some embodiments may therefore obtain a curve of the averaged measurement vs. stimulus amplitude in order to obtain information regarding the recruitment effected by each stimulus, and such information may be used for feedback control by the implant.

In some embodiments, the method of the present invention may be applied contemporaneously with administration of a drug, in order to gauge efficacy of drug delivery. For example, the implant may comprise or be operatively connected to a drug reservoir and drug delivery pump, with the pump being controlled by feedback based on CAP measurements.

According to another aspect the present invention provides a computer program product comprising computer program code means to make an implanted processor execute a procedure for measuring a neural response to a stimulus, the computer program product comprising computer program code means for carrying out the method of the first aspect.

The present invention recognises that when considering spinal cord stimulation, obtaining information about the activity within the spinal segment where stimulation is occurring is highly desirable. Observing the activity and extent of propagation both above (rostrally of) and below (caudally of) the level of stimulation is also highly desirable. The present invention recognises that in order to record the evoked activity within the same spinal segment as the stimulus requires an evoked potential recording system which is capable of recording an SCP within approximately 3 cm of its source, i.e. within approximately 0.3 ms of the stimulus, and further recognises that in order to record the evoked activity using the same electrode array as applied the stimulus requires an evoked potential recording system which is capable of recording an SCP within approximately 7 cm of its source, i.e. within approximately 0.7 ms of the stimulus.

In preferred embodiments the stimulus comprises a biphasic pulse, and the stimulus electrodes have no capacitors. In contrast to a monophasic pulse and capacitor arrangement, such embodiments permit the stimulus electrode current to be interrupted, or forced to zero, at those times where it would interfere with measurement. Omitting capacitors is also desirable in order to minimise the size of the implanted device.

BRIEF DESCRIPTION OF THE DRAWINGS

An example of the invention will now be described with reference to the accompanying drawings, in which.

DESCRIPTION OF THE PREFERRED EMBODIMENTS

Figure 1:
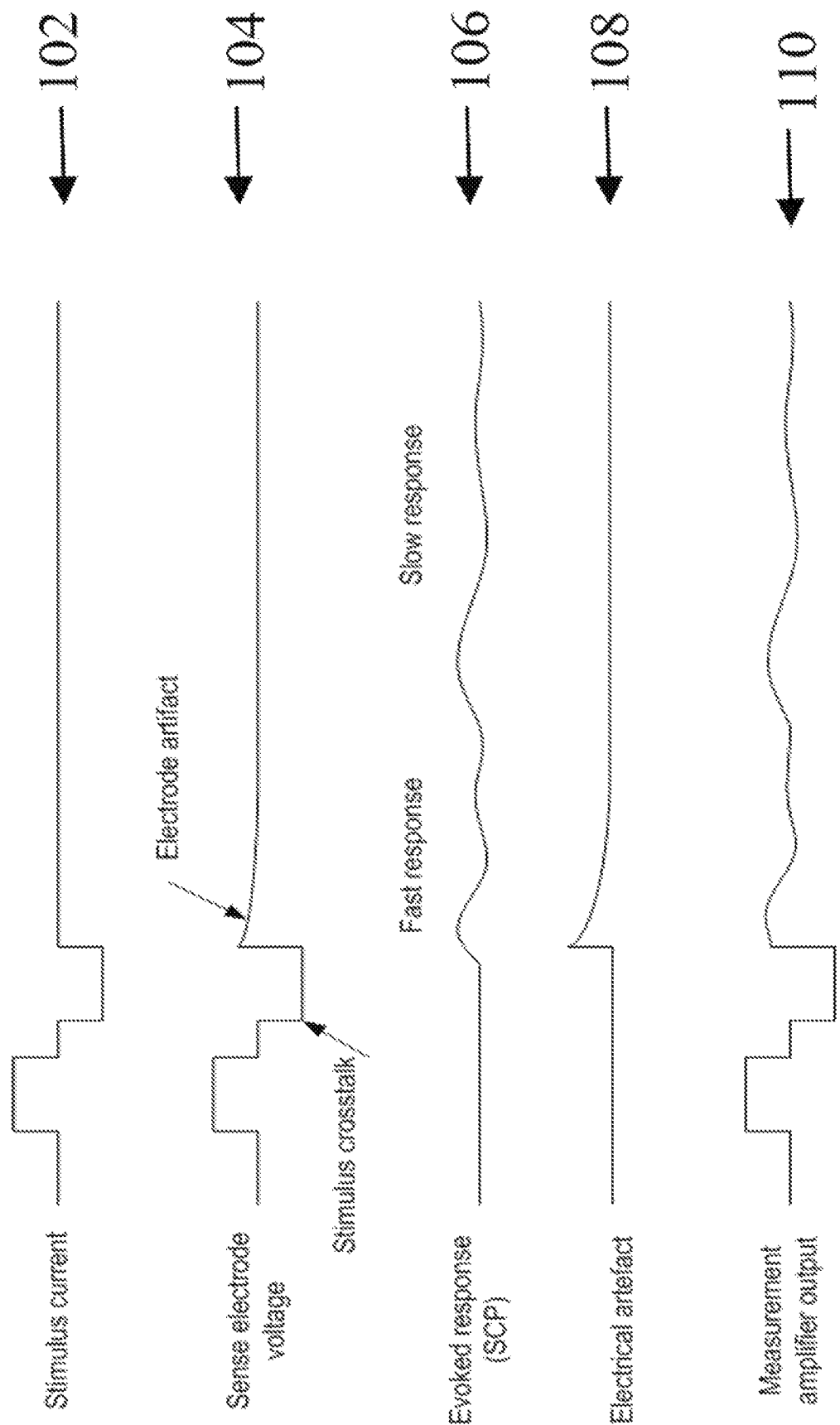
FIG. 1 illustrates currents and voltages which can contribute to SCP measurements.

FIG. 1 shows the currents and voltages that contribute to SCP measurements. These signals include the stimulus current 102 applied by two stimulus electrodes, which is a charge-balanced biphasic pulse to provide low artefact. Alternative embodiments may instead use three electrodes to apply a tripolar charge balanced stimulus. In the case of spinal cord stimulation, the stimulus currents 102 used to provide paraesthesia and pain relief typically consist of pulses in the range of 3-30 mA amplitude, with pulse width typically in the range of 100-400 µs, or alternatively may be paraesthesia-free such as neuro or escalator style stimuli. The stimuli can comprise monophasic or biphasic pulses.

The stimulus 102 induces a voltage on adjacent electrodes, referred to as stimulus crosstalk 104. Where the stimuli 102 are SCP stimuli they typically induce a voltage 104 in the range of about 1-5 V on a SCP sense electrode.

The stimulus 102 also induces electrode artefact, which is a residual voltage on an electrode resulting from uneven charge distribution on its surface. The electrode artefact is indicated in the voltage waveform 104 after cessation of stimulus crosstalk. The stimulus 102 disturbs the galvanic interface between the sense electrode and the tissue, so that after stimulus crosstalk in voltage 104 concludes, a voltage known as the electrode artefact continues on the electrode, as indicated in waveform 104 in FIG. 1. Electrode artefact is very difficult to measure, and depends on factors such as the stimulation pulse, the geometry of the electrodes and the bio-electrical nature of the tissue surrounding the electrodes. Electrode artefact can have a typical value of 500 µV at a time 50 µs after stimulation ceases. Electrode artefact is difficult to measure because it is indistinguishable from electrical artefact, the latter being caused by the amplifier's exposure to the high stimulation voltages. Further, the causes of electrical artefact can be subtle, and therefore hard to identify and eliminate.

An appropriate stimulus 102 will also induce nerves to fire, and thereby produces an evoked neural response 106. In the spinal cord, the neural response 106 has two major components: a fast response lasting ~2 ms and a slow response lasting ~15 ms. The slow response only appears at stimulation amplitudes which are larger than the minimum stimulus required to elicit a fast response. The amplitude of the evoked response seen by epidural electrodes is typically no more than hundreds of microvolts, but in some clinical situations can be only tens of microvolts.

In practical implementation a measurement amplifier used to measure the evoked response does not have infinite bandwidth, and will normally have infinite impulse response filter poles, and so the stimulus crosstalk 104 will produce an output 108 during the evoked response 106, this output being referred to as electrical artefact.

Electrical artefact can be in the hundreds of millivolts as compared to a SCP of interest in the tens of microvolts. Electrical artefact can however be reduced by suitable choice of a high-pass filter pole frequency.

The measurement amplifier output 110 will therefore contain the sum of these various contributions 102-108. Separating the evoked response of interest (106) from the artefacts 104 and 108 is a major technical challenge. For example, to resolve a 10 µV SCP with 1 µV resolution, and have at the input a 5V stimulus, requires an amplifier with a dynamic range of 134 dB. As the response can overlap the stimulus this represents a difficult challenge of amplifier design.

FIG. 2A, FIG. 2B, FIG. 2C, FIG. 2D, and FIG. 2E are schematic diagrams of the five phases of operation of a sample and hold (S/H) measurement amplifier in accordance with one embodiment of the present invention. The stimulus and measurement circuitry 200 comprises a buffer amplifier 206 that is always connected to the sense electrode 202 such that there is no switch between the sense electrode 202 and the buffer amplifier 206. The output of the buffer amplifier 206 drives a sample and hold circuit 208, followed by a high gain amplifier 210 with unity gain at DC. The front-end amplifier 206 has sufficiently wide bandwidth that it can follow the voltage induced on the sense electrodes 202 by the stimulus pulse, and settle before the SCP begins. A current source 212 can be selectively connected to stimulus electrodes 204 to deliver a stimulus. The stimulus electrodes 204 and sense electrode 202 are in the same electrode array of a single implanted device.

The stimulus and measurement circuitry 200 operates to obtain a SC measurement using five phases. The first phase shown in FIG. 2A open circuits the stimulus electrodes 204 and connects the sense electrode 202 to the measurement amplifier 210 by setting the sample and hold circuit to "sample". The first phase shown in FIG. 2A allows the amplifier chain 206, 210 to settle, with no disturbance from the stimulating electrodes 204.

Figure 2A:
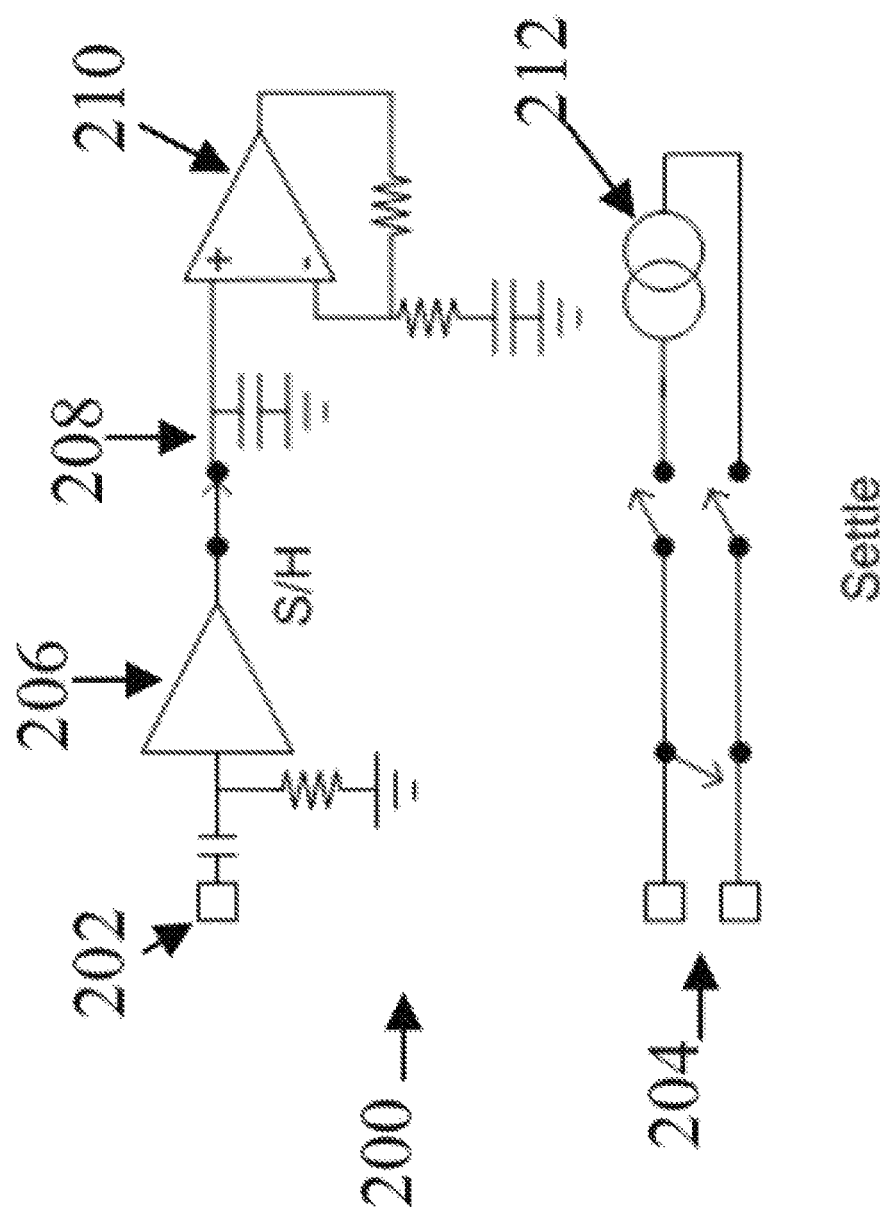
FIG. 2A illustrates the circuitry of one embodiment of the present invention during the settle phase of a measurement cycle.
Figure 2B:
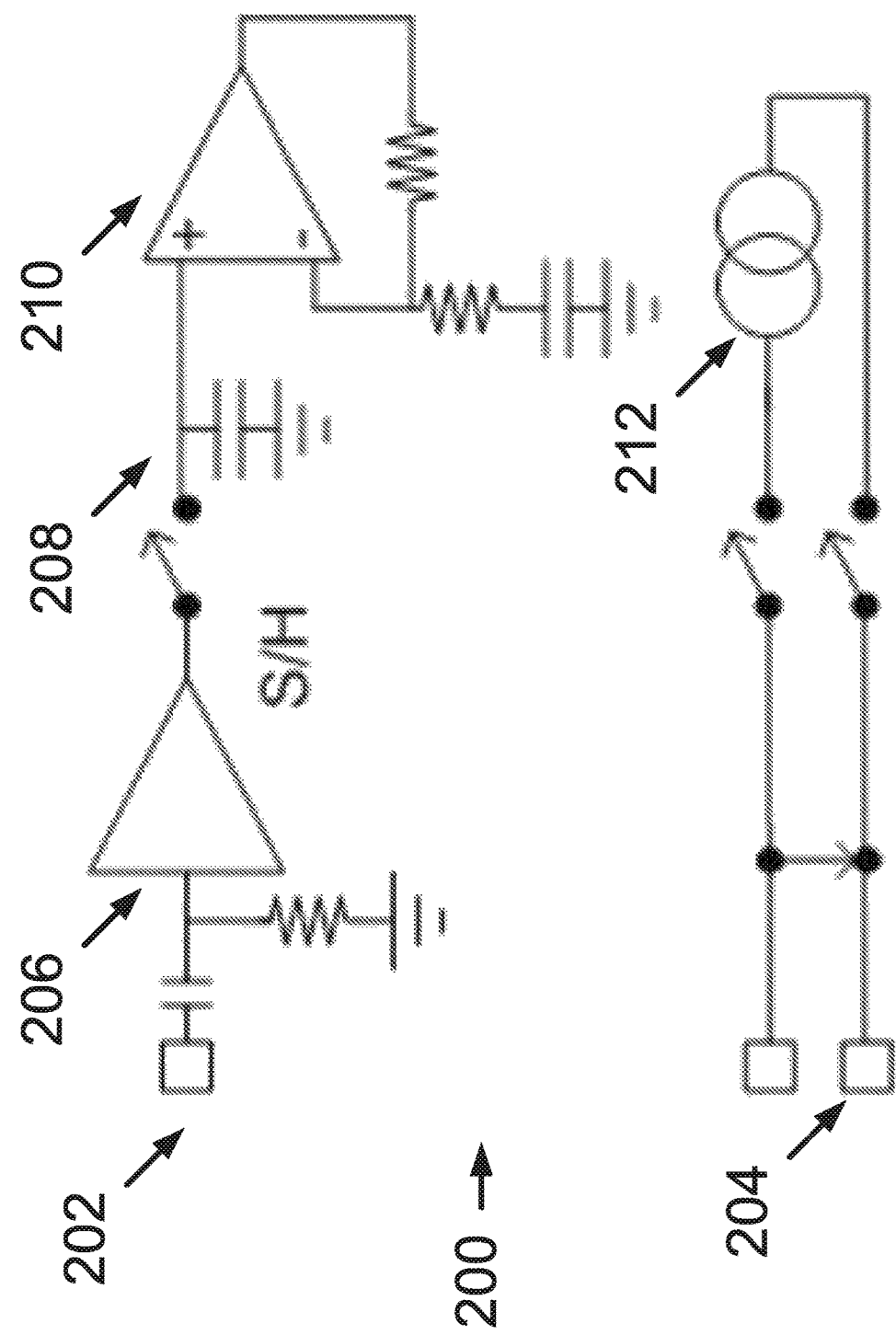
FIG. 2B illustrates the circuitry of one embodiment of the present invention during the charge recovery phase of a measurement cycle.

In the second phase shown in FIG. 2B, the stimulus electrodes 204 are short circuited to each other. This allows the stimulating electrodes 204 to recover charge, so as to avoid DC injection to the tissue as is required for electrical implants. During this phase, the sample-and-hold 208 is set to "hold" so that charge transfer on the stimulus electrodes 204 does not disrupt the measurement amplifier 210.

Figure 2C:
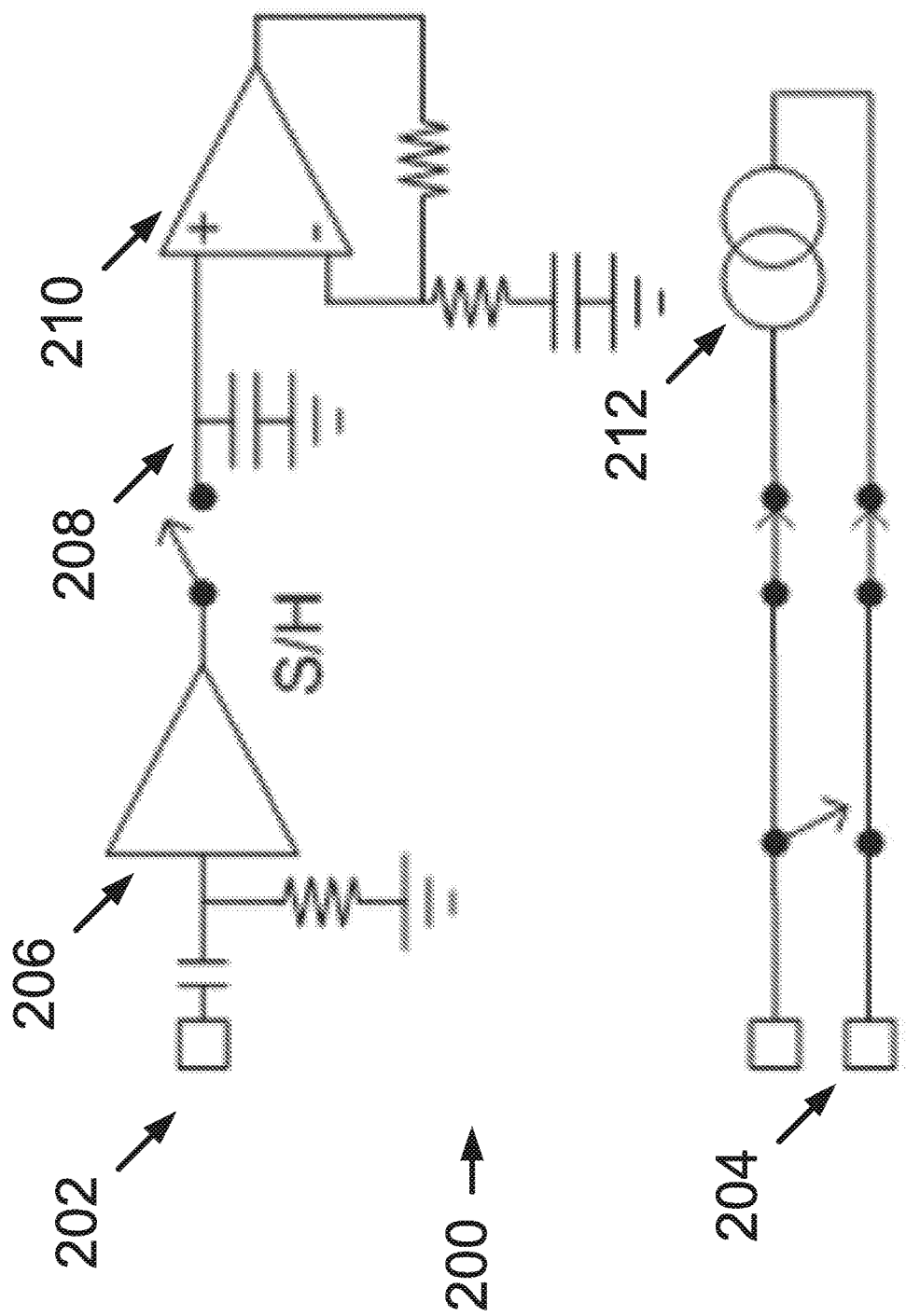
FIG. 2C illustrates the circuitry of one embodiment of the present invention during the stimulate phase of a measurement cycle.

In the third phase shown in FIG. 2C, the stimulation is applied. The stimulus electrodes 204 are switched to the current source 212, and the sample-and-hold 208 is set to "hold" so that the large stimulus crosstalk seen on electrode 202 is not presented to the measurement amplifier 210.

Figure 2D:
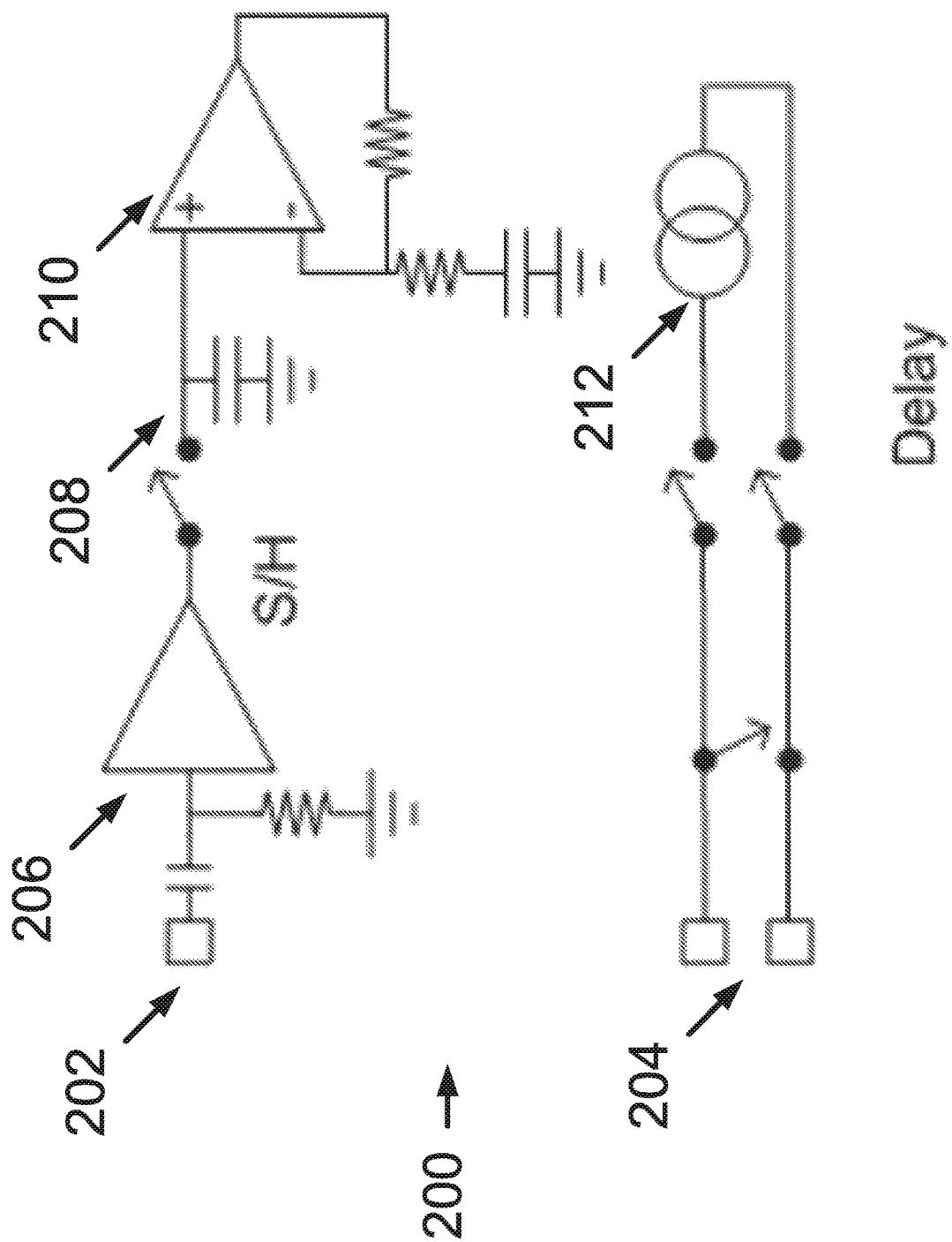
FIG. 2D illustrates the circuitry of one embodiment of the present invention during the delay phase of a measurement cycle.

The fourth phase shown in FIG. 2D provides for a post-stimulus delay. In this phase the stimulus electrodes 204 are open circuited, and the sample-and-hold remains in the "hold" position, to allow the electrodes 202, 204 settle towards equilibrium, as defined by bio-electrical conditions.

Figure 2E:
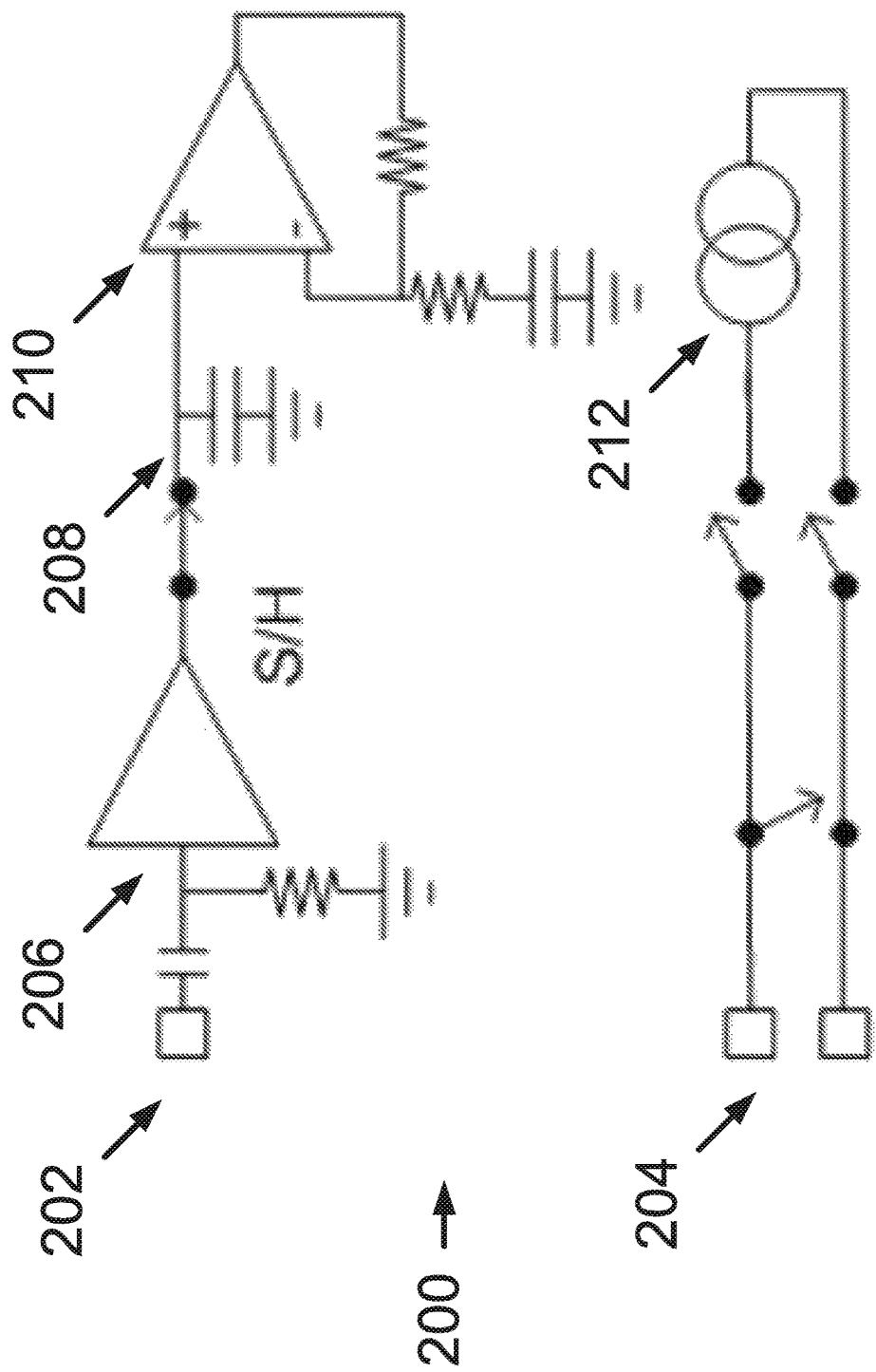
FIG. 2E illustrates the circuitry of one embodiment of the present invention during the measure phase of a measurement cycle.

Finally, in the fifth phase shown in FIG. 2E, the SCP present at sense electrode 202 is measured by switching the sample-hold 208 to "sample".

When performing repeated measurement cycles in this fashion, it is noted that the switch positions are the same in the phase 1 "settling" and the phase 5 "measuring" states. Thus, the state of phase 5 is maintained, by virtue of a subsequent phase 1, until the electrodes and circuitry are in equilibrium, even after the time that useful SCP data is no longer present or being captured. Such embodiments thus provide a greater length of the "settle" state.

Figure 3:
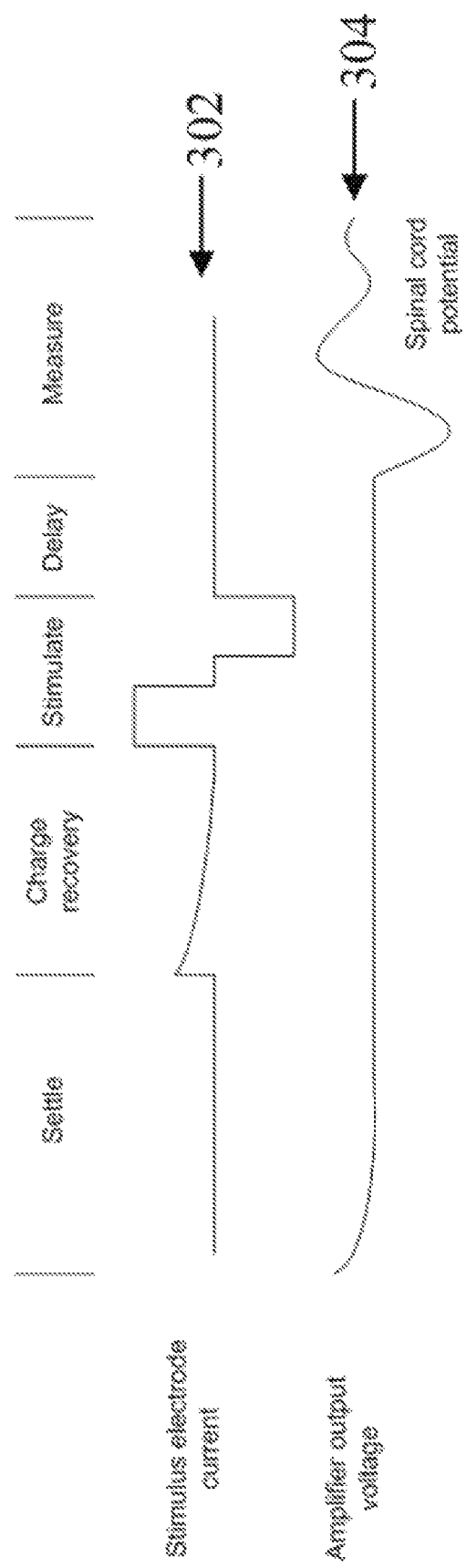
FIG. 3 illustrates idealised waveforms arising in the circuit of FIG. 2 during each phase of the measurement cycle.

FIG. 3 shows idealised waveforms arising during the SCP measurement process of FIG. 2. FIG. 3 illustrates the current 302 of stimulus electrodes 204, and the output voltage 304 of amplifier 210, during each of the five phases of the measurement cycle. Importantly, it can be seen that phase 1 permits the amplifier bias point to settle to a steady state as defined by bio-electrical conditions at the sense electrode, while phases 2-4 do not disrupt the amplifier 210 bias point.

An advantage of this circuit is that in the phase 2 equilibration, the circuitry around amplifier 210 is a low-pass filter, and is therefore relatively immune to noise and input transients. This also allows the amplifier 210 to accumulate its bias point over successive measurement cycles, as it does not need to be reset for each cycle. Moreover, because of the buffer 206 before the sample/hold 208, the input-referred effect (i.e. the effect upon sense electrode 202) of the charge injection into the sample/hold 208 is lower.

In the embodiment of FIG. 2, the sense electrode 202 is never shorted to the stimulus electrodes 204, recognising that this creates dis-equilibrium in the sense electrodes and adds artefact, rather than having the effect of creating equilibrium as previously thought. In some embodiments, it may be possible to overlap the "settle" (equilibrate) phase of FIG. 2A, and the "charge recovery" phase of FIG. 2B, although it would be expected that the artefact would be higher, and the time taken to reach equilibrium longer.

Figure 4:
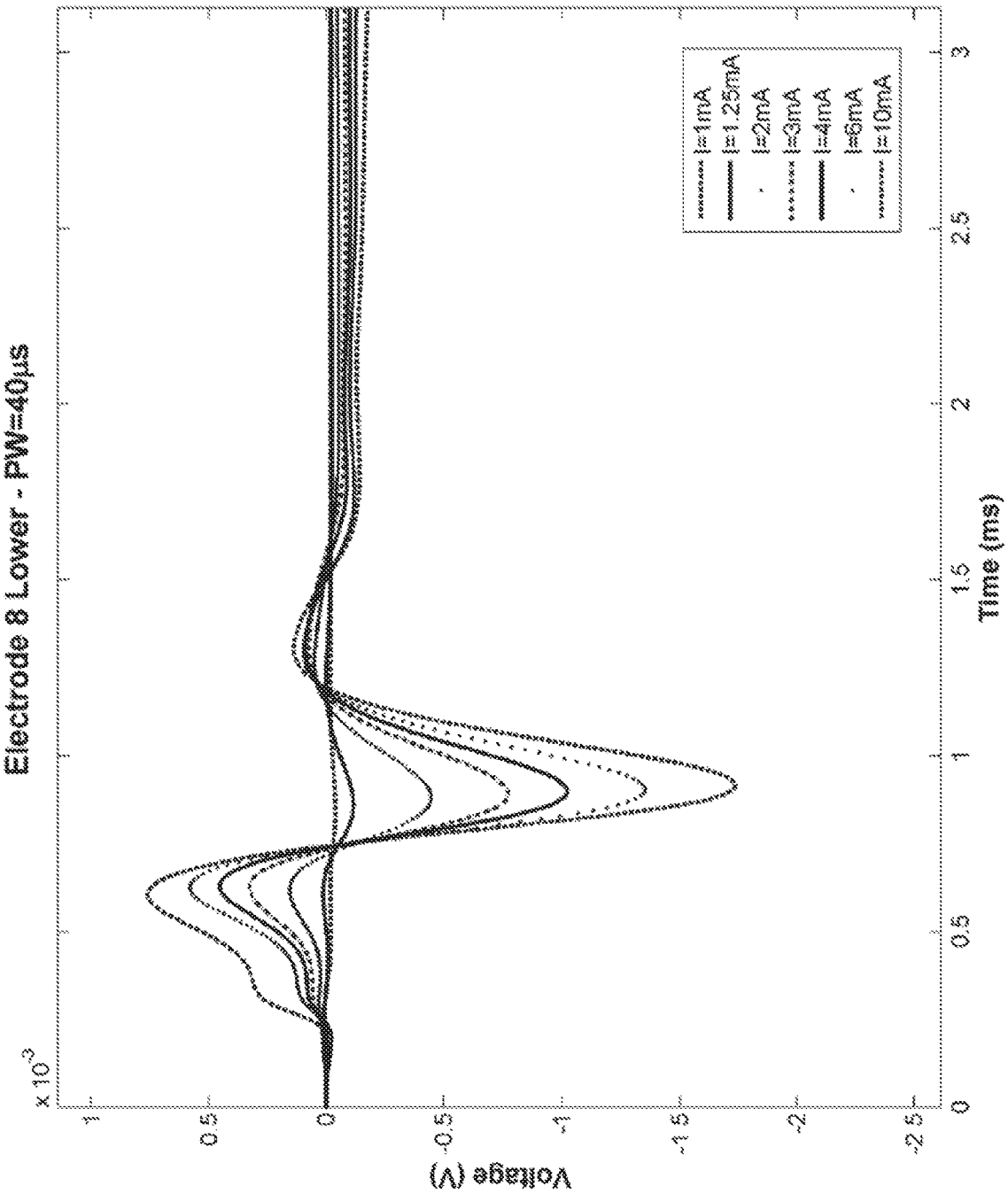
FIG. 4 illustrates SCP measurements made using the embodiment of FIG. 2.

FIG. 4 is a plot of 22 separate measurements of ovine SCP made using the embodiment of FIG. 2. The measurements were obtained sequentially for differing stimuli, the stimuli comprising biphasic current pulses of 40 µs pulse width and a current amplitude which varied from 0-10 mA. The measurements were then plotted on a single chart to produce FIG. 4. The recorded signals consist of the neural response and a small electrode artefact. The neural response is tri-phasic, consisting of a positive P1 peak followed by a negative N1 peak and then a secondary positive P2 peak.

The neural response morphology in FIG. 4 is characteristic of extracellular recordings of axonal compound action potentials. The first phase P1 is dominated by the capacitive current due to the initial membrane depolarization. Phase 2 is dominated by Na+ ion current and is negative due to the influx of Na+ ions during the neuronal membrane action potential. The third phase is positive due to the K+ ion conduction during repolarization.

The waveforms of FIG. 4 have lower dynamic range and simpler morphology than measurements produced by previous approaches, due to the absence of stimulus crosstalk and reduced artefact. When wishing to provide a system built on an implanted integrated circuit, wide dynamic range amplifiers are difficult to design, as are signal processing systems for feature extraction. Beneficially, the nature of the measured waveforms shown in FIG. 4 permits, for example, a circuit for extracting the peak-to-peak SCP amplitude to have fewer components than would be required to operate upon the waveform produced by previous approaches. Thus the techniques of the present invention for artefact reduction greatly assist in building a practical implanted, evoked response feedback system.

Moreover, it is notable that in this case of a 40 µs pulse width the measurement system is settled and ready to record prior to onset of the evoked CAP. The sense electrode was less than 50 mm from the stimulus electrode, and a post-stimulus delay of 50 µs was observed before the measurement amplifier was switched in to obtain the recordings shown in FIG. 4. As can be seen in FIG. 4 the largest peak to peak response was about 2.4 mV, significantly less than the voltage present when applying a 10 mA stimulus. Moreover, the epidural space is much smaller in sheep than in humans, and so the electrode is expected to be closer to the ovine neural tissue and the magnitude of the sensed tri-phasic potentials is correspondingly higher in the sheep than is expected for humans, emphasizing the difficulty of making such recordings.

Figure 5:
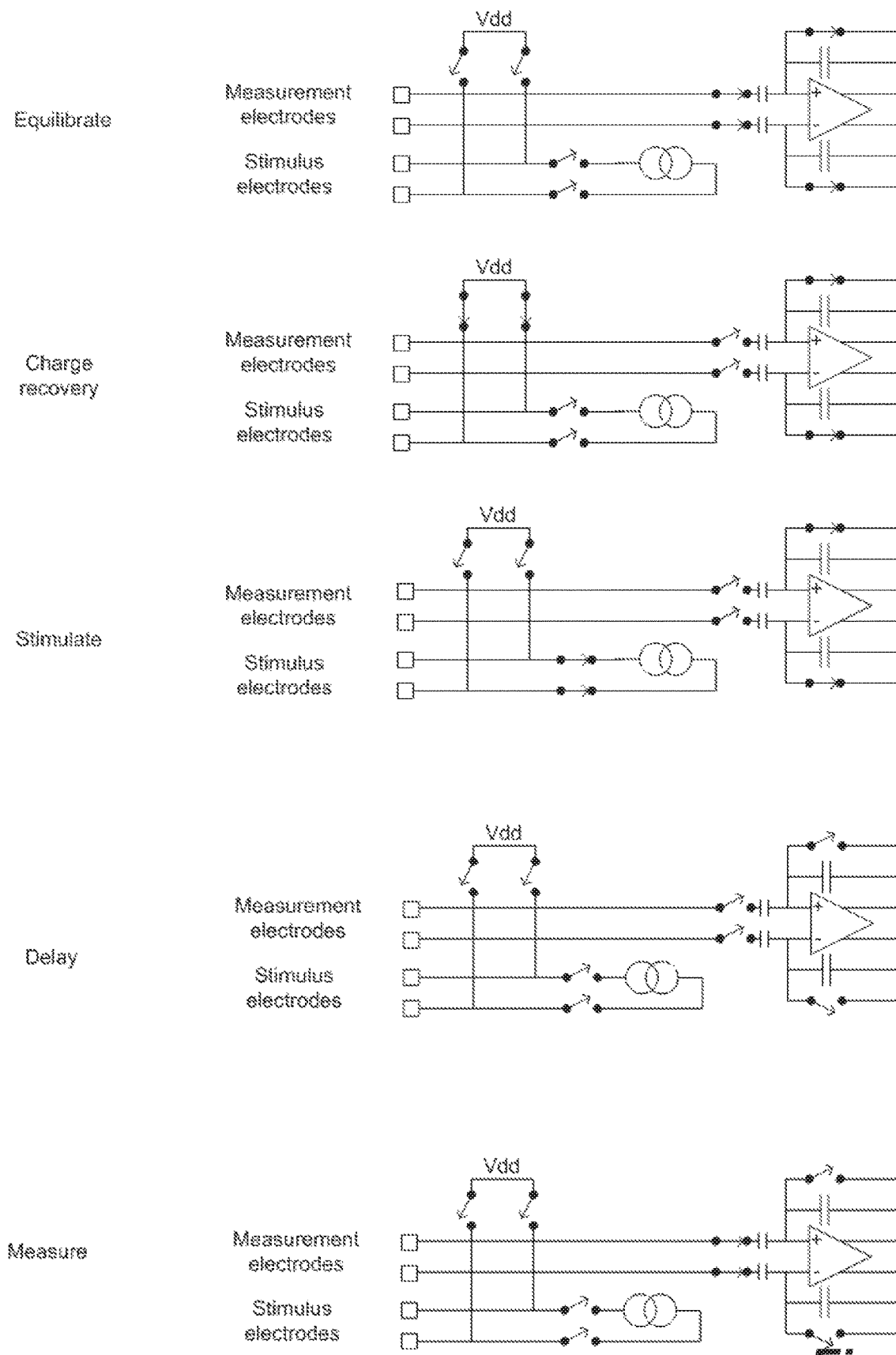
FIG. 5 illustrates the circuitry of an alternative embodiment of the invention implementing differential CAP measurements.

FIG. 5 illustrates the circuitry of an alternative embodiment of the invention in which a differential measurement amplifier is used, and charge recovery is via a voltage rail $V_{dd}$. As can be seen, in accordance with the present invention the measurement phases are carried out in a corresponding manner despite the use of different hardware.

Figure 6:
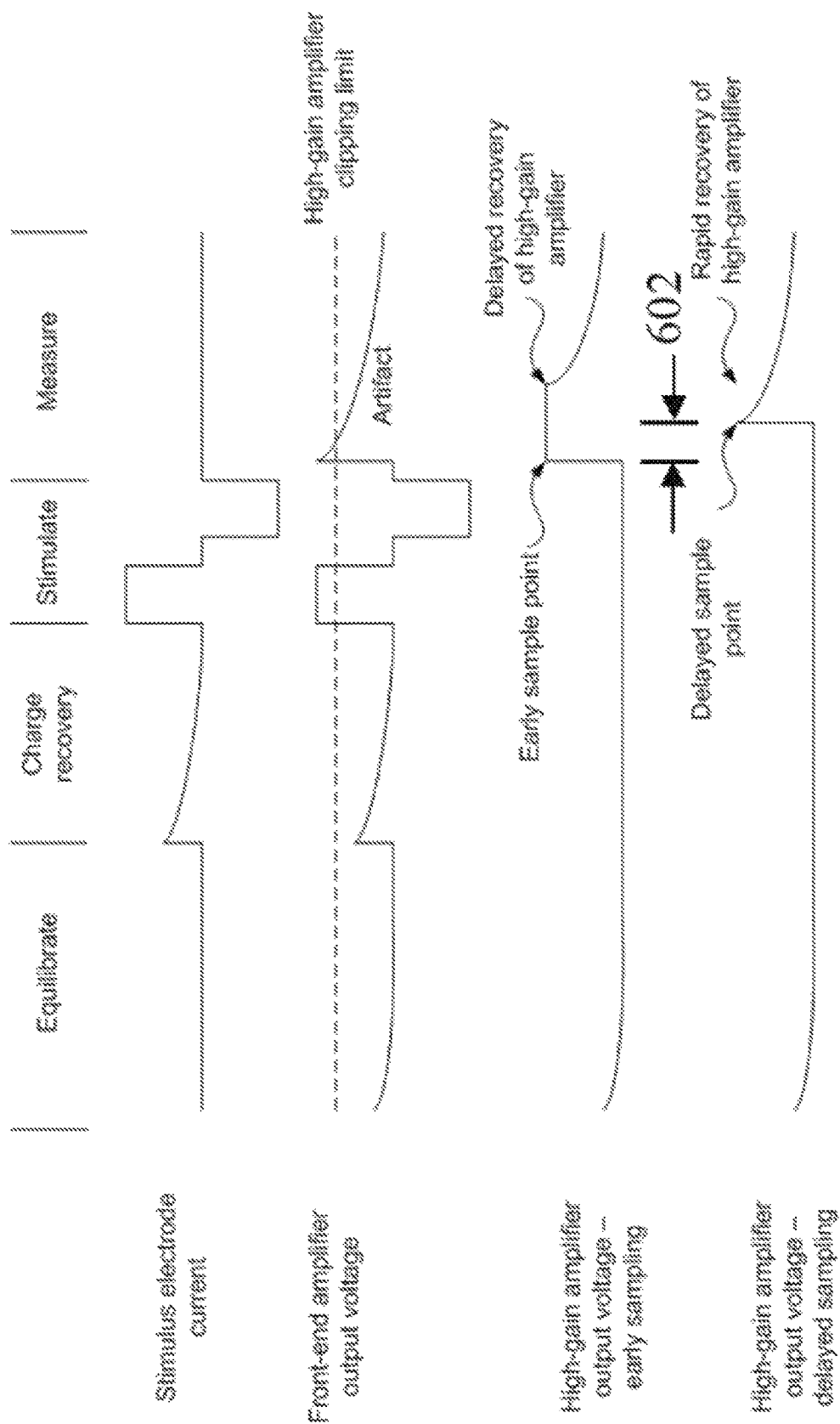
FIG. 6 illustrates delayed activation of a measurement amplifier to avoid clipping.

In the embodiments of either FIG. 2 or FIG. 5, artefact can cause the high-gain measurement amplifier 210 to clip, and the amplifier can subsequently be slow to recover. However, in preferred embodiments the sample point, being the transition from the "stimulate" to "measure" phases, is delayed, allowing clipping to be avoided. FIG. 6 illustrates the manner of determining a suitable delay 602, which is often in the range of 50-200 µs, noting that the fast response typically concludes within about 2 ms. Such embodiments may permit use of a higher amplifier gain than would otherwise be the case. In particular, a variable delay and increased amplifier gain may be particularly apt in circumstances where high-gain is desired, and parts of the SCP of interest do not immediately follow the stimulation. Thus, delaying the start of measurement will avoid the side effects of clipping.

Figure 7:
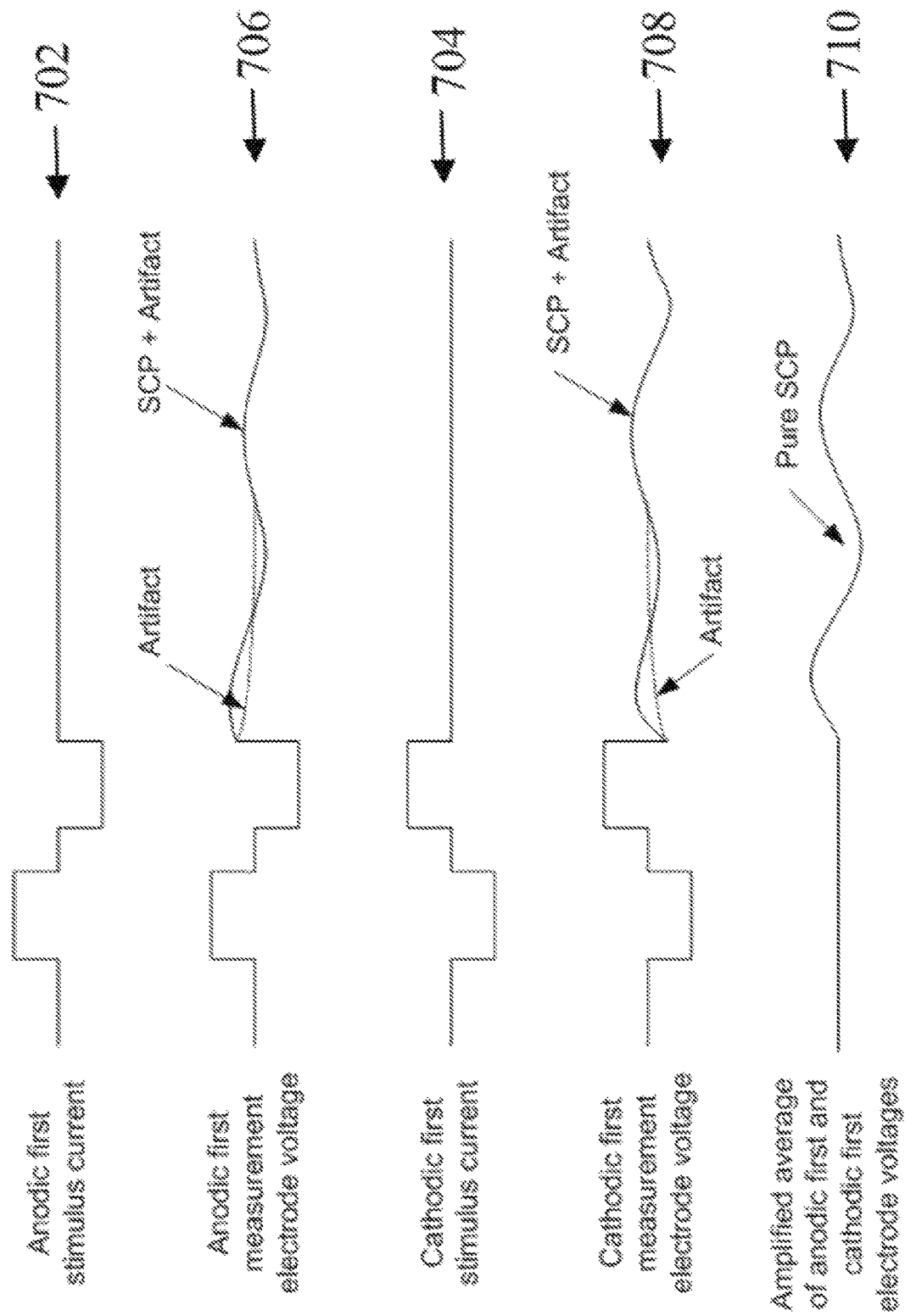
FIG. 7 illustrates an embodiment in which alternate phased stimuli are used to obtain an averaged CAP measurement.

In another embodiment of the invention shown in FIG. 7, a method to eliminate artefact from an SCP measurement is to alternate the phase of stimulus waveforms and take an average of obtained measurements. This method is effective when the stimulus electrodes have different area. For example, in tripolar stimulation a central electrode is driven anodically in the first phase and consists of a single electrode of the array, whereas the electrode driven cathodically in the first phase consists of two electrodes of the array connected in parallel. The electrodes in parallel would usually be on either side of the other stimulating electrode. Similarly, if stimulation were between one electrode in the epidural space and one electrode elsewhere, such as being attached to an implant body, then a mode of stimulation referred to as "monopolar" stimulation is obtained.

FIG. 7 shows the stimulus current for a positive "anodic-first" stimulus 702, and the stimulus current for a negative "cathodic first" stimulus 704. In this embodiment these are applied in succession with respective CAP measurements obtained after each stimulus. The respective measurement electrode voltages 706 and 708 arising from each such stimulus are also shown. It will be observed where indicated in waveforms 706, 708 that the artefacts from each of the two stimuli are of substantially identical magnitude, but opposite sign. In most situations it will be found that the artefact polarity depends on the stimulus polarity. An example of this would be electrical artefact caused by the high-pass poles of the front-end amplifier 206. Clearly, either phase could be used for stimulating nervous tissue, though their effects will differ.

In contrast, the positive and negative phase stimuli 702, 704 produce SCPs of differing amplitudes, but approximately similar shape and importantly of similar polarity, as this is determined by the anatomy and physiology of the spinal cord nerve fibre membranes. Thus, when the voltages 706, 708 resulting from the positive and negative phase stimuli 702, 704 are recorded, and averaged, the opposite phase stimulation artefacts substantially cancel, leaving the SCP or a combination of the two SCPs 710. Note that in practical situations, the artefact can have much higher amplitude than the SCP, making it much harder to detect the SCP than is apparent from FIG. 7.

The response of the spinal cord to these two polarities of stimulation are referred to as the "anodic" and "cathodic" SCP responses, as referred to the electrode considered to be that closest to the recording electrode. I.e. anodic tripolar stimulation makes the central stimulating electrode anodic in the first phase of stimulus. Usually cathodic stimulation has a lower threshold for neural activation than is the case for anodic stimulation. Nevertheless, the SCP polarity is independent of whether the stimulus is anodic 702 or cathodic 704.

Figure 8A:
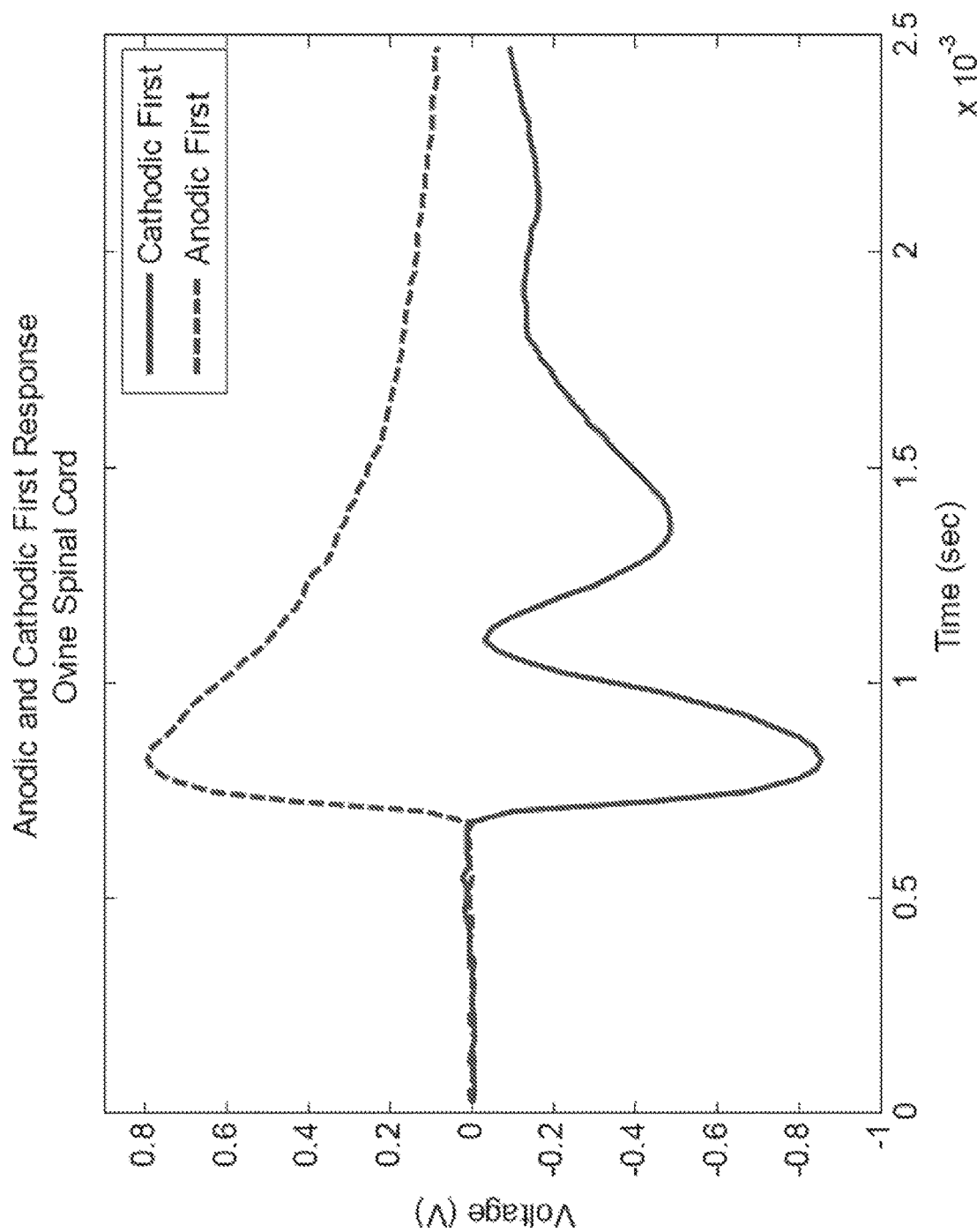
FIG. 8a illustrates the "anodic first" and "cathodic first" CAP responses induced by the method of FIG. 7.

FIG. 8a illustrates spinal cord measurements obtained in response to anodic and cathodic monophasic stimulations, respectively, the stimuli being of equal amplitude. Note that the measurement obtained in response to the anodic stimulation lacks the characteristic P1-N1-P2 form, indicating that the anodic stimulation did not evoke a neural response in this case. In contrast, the measurement obtained in response to the cathodic stimulus exhibits a significant evoked neural response.

Figure 8B:
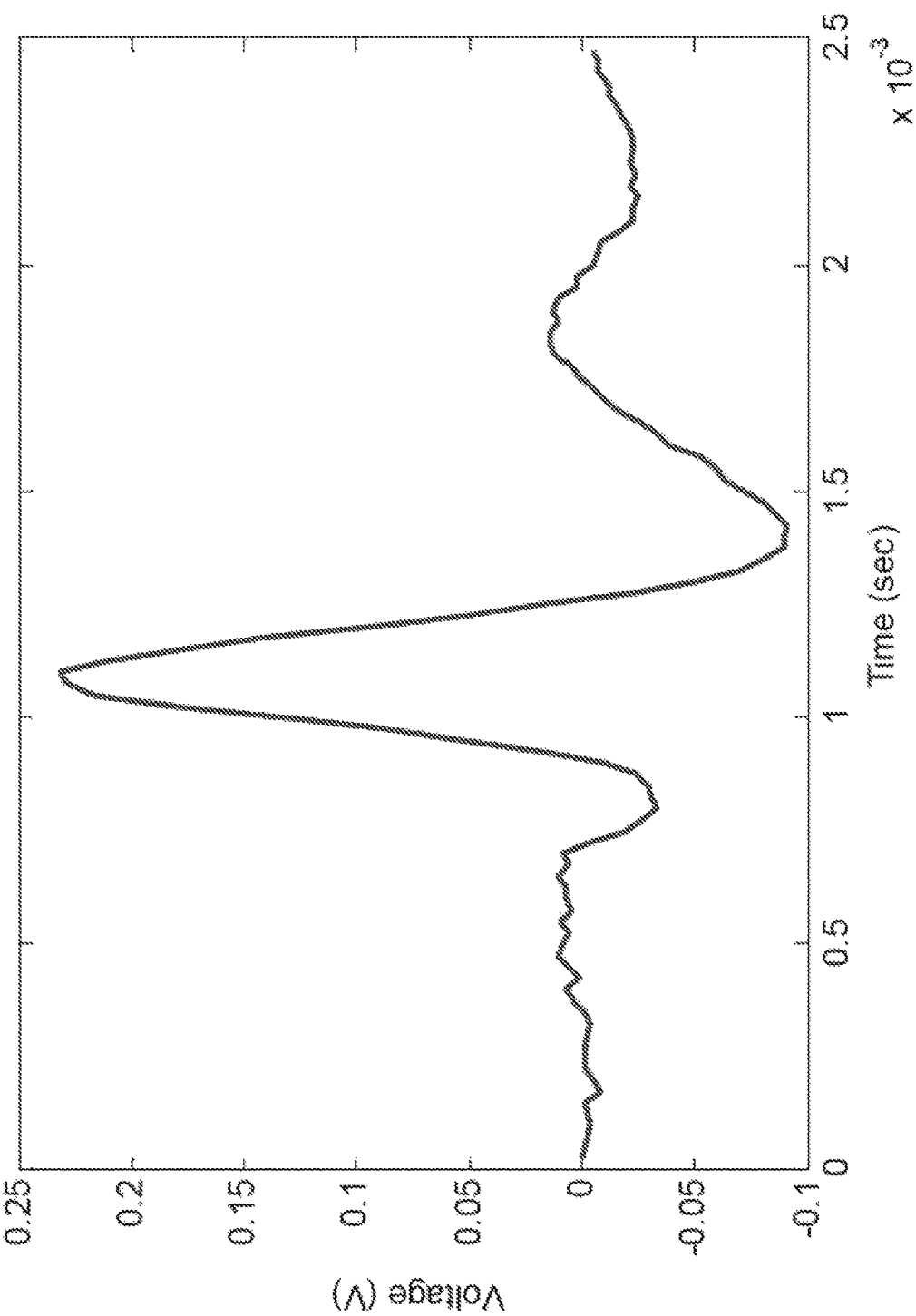
FIG. 8b illustrates the averaged measurement obtained by the method of FIG. 7.

FIG. 8b shows an average of the two responses in FIG. 10a. As can be seen, while the characteristic form of the SCP has been altered, the artefact is essentially removed as stimuli of opposite polarity and equal amplitude produce artefact of opposite polarity and equal amplitude, which cancel when averaged.

Figure 9:
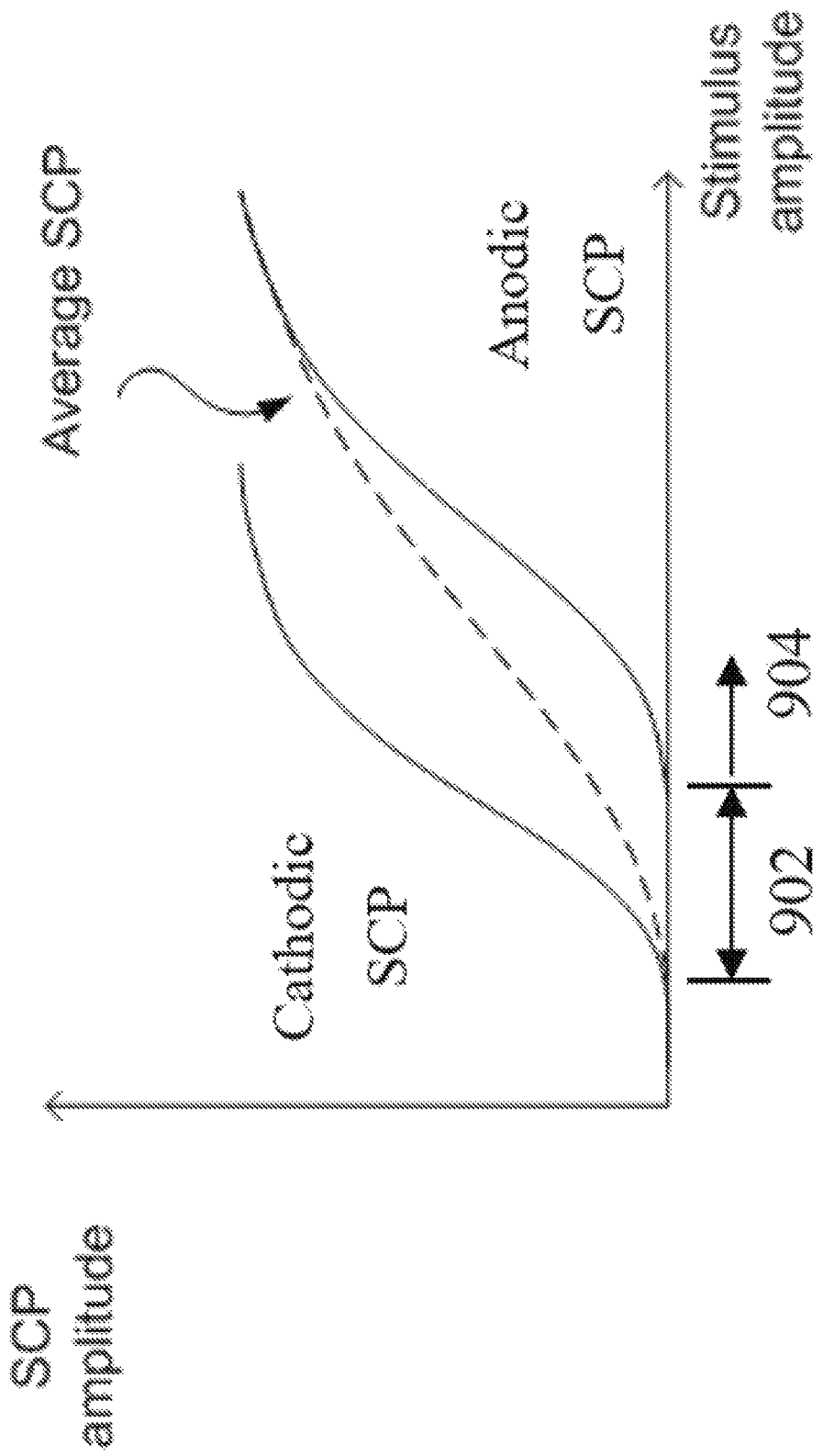
FIG. 9 illustrates the CAP response to anodic-first and cathodic-first stimuli, respectively, with increasing stimulus amplitude.

This embodiment of the invention further recognises that the averaged waveform of FIG. 8b can be used to obtain a range of information despite the atypical SCP form. In this regard, FIG. 9 illustrates SCP growth curves against stimulus amplitude, for both anodic and cathodic monophasic stimuli. FIG. 9 also shows the growth behaviour of the average SCP against stimulus amplitude. It can be seen from FIG. 9 that the threshold of the average response is identical to the threshold of the more sensitive response for cathodic stimulation.

When the stimulus amplitude is in the range 902 such that only the cathodic stimulus produces an SCP, then the averaged SCP waveform would have a normal SCP morphology but would be half the amplitude compared to a true cathodic SCP due to the averaging. In the region 904 where both the anodic and cathodic responses contribute to the averaged SCP, the resultant averaged SCP waveform will have morphology in between the two measurements. It would not directly represent an SCP, but rather the average of two different SCPs. Nevertheless, this waveform could still be valuable for example in implementing an automatic control loop for stimulation adjustment, as it gives a value proportional to neural recruitment.

It is further to be noted that the principle portrayed by FIG. 9 applies in a similar manner to other stimulus polarities. For example, some embodiments may stimulate with a tripolar arrangement having a centre electrode operating as a cathode and having two edge electrodes, being those immediately to each side of the centre electrode, operating as anodes. This tripolar arrangement means that the recovery charge is shared between the two edge electrodes. For a biphasic tripolar stimulus the cathodic charge on the 2nd phase is shared between two electrodes and thus is half that on the first phase. Thus the principle shown in FIG. 9 is true for tripolar stimulation, at least up to the point where the current is twice the threshold current at which point the edge electrodes' currents are each at the threshold and will thus start to generate action potentials.

Some embodiments of the invention, such as the embodiment of FIG. 5, may use differential amplifiers so as to detect the voltage difference between two sense electrodes. Differential amplifiers simplify the task of separating electrode artefact. If they are connected to electrodes with similar area, and separated from the stimulation electrodes in a similar manner, then they receive similar levels of electrode artefact and this will be removed when their difference voltage is obtained. However, in such a system the voltage recorded by the amplifier is the difference between the voltages at two points along a bundle of neurons, and can thus be difficult to interpret. When making SCP measurements, it is preferable to use single-ended amplifiers as they more accurately measure the SCP, and they are more sensitive in measuring the SCP.

Figure 10:
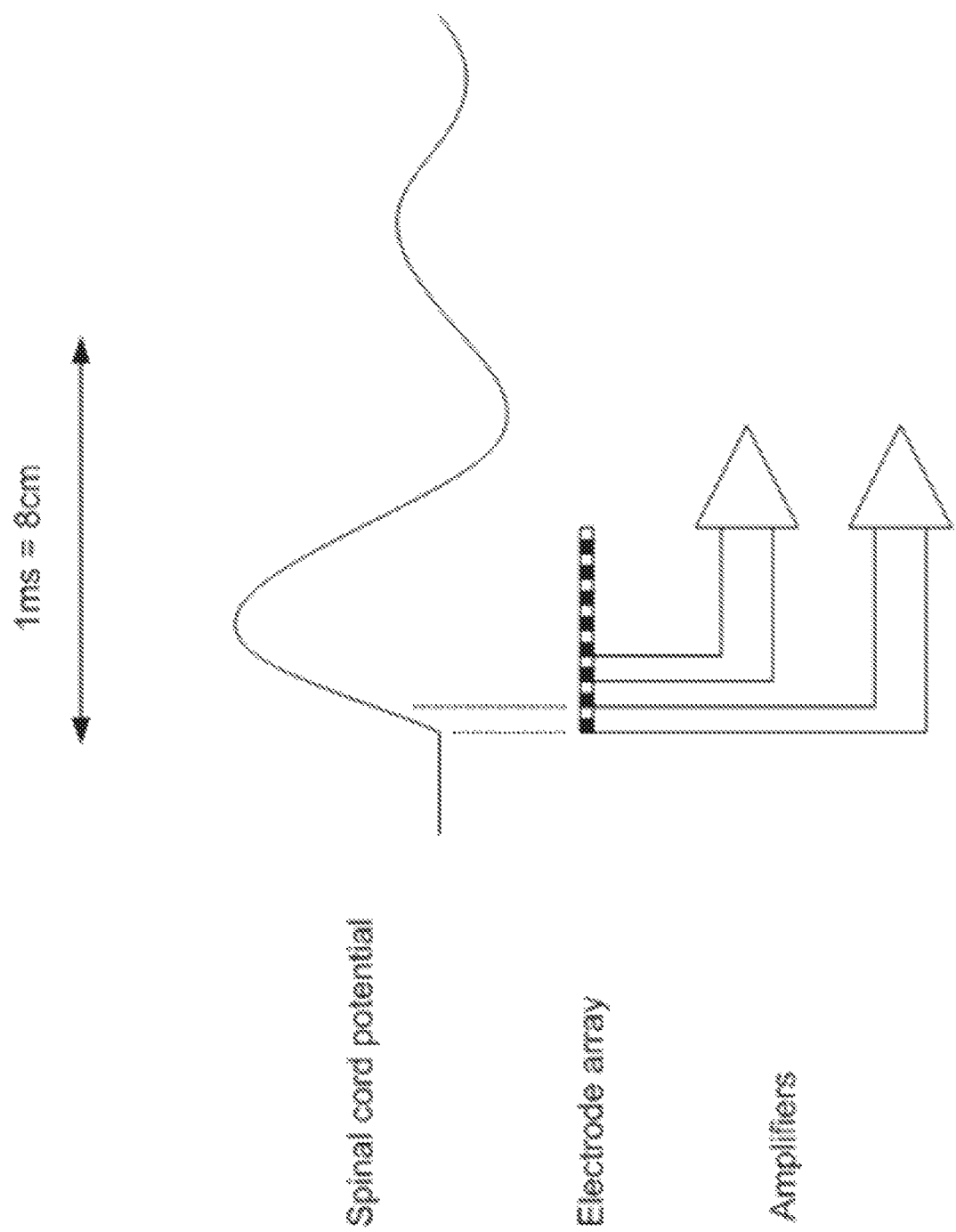
FIG. 10 illustrates the nature of differential CAP measurements in the spinal cord.

Differential amplifiers are often used because they provide a means to reduce electrode artefact, when other means have been insufficient. However, FIG. 10 illustrates a problem of measuring SCPs with differential amplifiers. It shows a spinal cord potential. As this potential travels along the spine at a velocity, which can be as high as 80 m·s$^{-1}$, it can also be considered as a spatial wave. Given that a peak-to-peak cycle of the fast response of an SCP typically lasts for 1 ms, the wave will travel 8 cm in this time. Using this 1 ms=8 cm scale, a 5 cm electrode array is drawn alongside the SCP in FIG. 10. Connected to this electrode array are two amplifiers configured to make differential SCP measurements from separate pairs of sense electrodes. As can be seen from FIG. 10, the difference between the voltages on the adjacent electrodes will be quite small and significantly smaller than the peak to peak amplitude of the SCP, and thus more susceptible to electrical noise generated by the amplifier. The output of the amplifier will approximate the differential of the SCP, and thus be harder to interpret than a simple measure of the SCP itself. If measuring evoked SCPs with a micro-package stimulator design, for example in a system using a two-wire bus, differential measurements between non-adjacent electrodes are not possible. Further, if wishing to measure the slow response of the SCP, which has a period of about 6 ms and correspondingly reduced signal gradients, differential measurements are even more difficult to effect. Thus it will be appreciated that single-ended measurements are preferable, as long as artefact can be kept at a sufficiently low level.

With the measurement sequence of the present invention, the artefact is reduced so that some embodiments may instead use a single-ended amplifier, even in situations where previously they would have suffered from too much electrode artefact. Moreover, trials to date show that recording can be initiated with an extremely short time interval from cessation of the stimulus, permitting the same electrode array to be used for recording and stimulation, and even permitting recordings to be made on the electrode immediately adjacent to the stimulus electrode in an electrode array with electrode spacings of less than 10 mm.

Single ended amplifiers have the further advantage that they consist of fewer capacitors and amplifier components than differential amplifiers, so will take up less space on a silicon chip, which is a significant benefit when intended for use in an implanted system with many electrodes and where the silicon area for each amplifier is limited.

Preferred embodiments of the invention may comprise a separate amplifier chain (e.g. 206, 208, 210, see FIG. 2) for every electrode, organised in parallel manner, permitting simultaneous recording of a single CAP from multiple sense electrodes in parallel, and also eliminating the switching noise arising in systems which switch the sense electrode to a shared measurement amplifier.

Figure 11A:
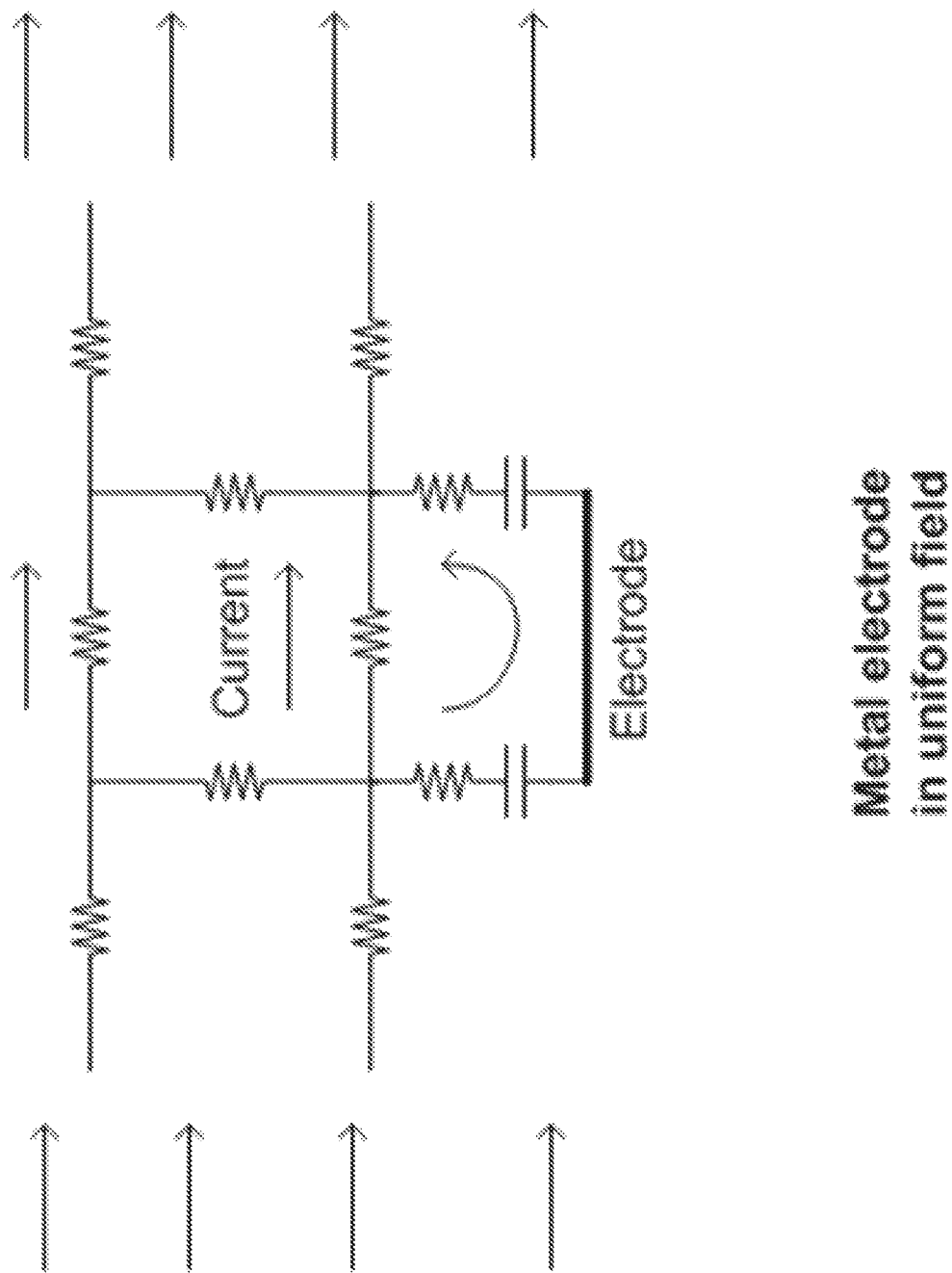
FIG. 11A illustrates a model of a metal electrode in a uniform electric field.

Further embodiments of the invention may employ divisible electrodes, as discussed below with reference to FIG. 11A, FIG. 11B, FIG. 11C, and FIG. 11D. When considering electrode artefact in particular, the sources of electrode artefact are relatively poorly understood. The surface of a metal electrode can be modelled as an RC network. For an accurate model, an infinite-phase element is required, but for the explanation of artefact a simple RC model will suffice, as shown in FIG. 11A. A conductive solution can be modelled as a mesh of resistors. Where a conductive solution meets a piece of metal of finite dimensions, the metal provides an alternative conduction path to the solution. This charges the electrode-to-tissue capacitances at the "ends" of the electrodes, with opposite polarities. The electrode does not acquire net charge, but it does cease to be in equilibrium. After the external current ceases, then the electrode will pass current through the solution as it re-equilibrates for a short time after the stimulus. This current will affect the potential of another electrode in the solution, and in the case of multi-electrode arrays a unique such current will arise at every electrode in response to local conditions experienced at that electrode. The cumulative impact of such re-equilibration currents is seen by a sense electrode as electrode artefact.

Figure 11B:
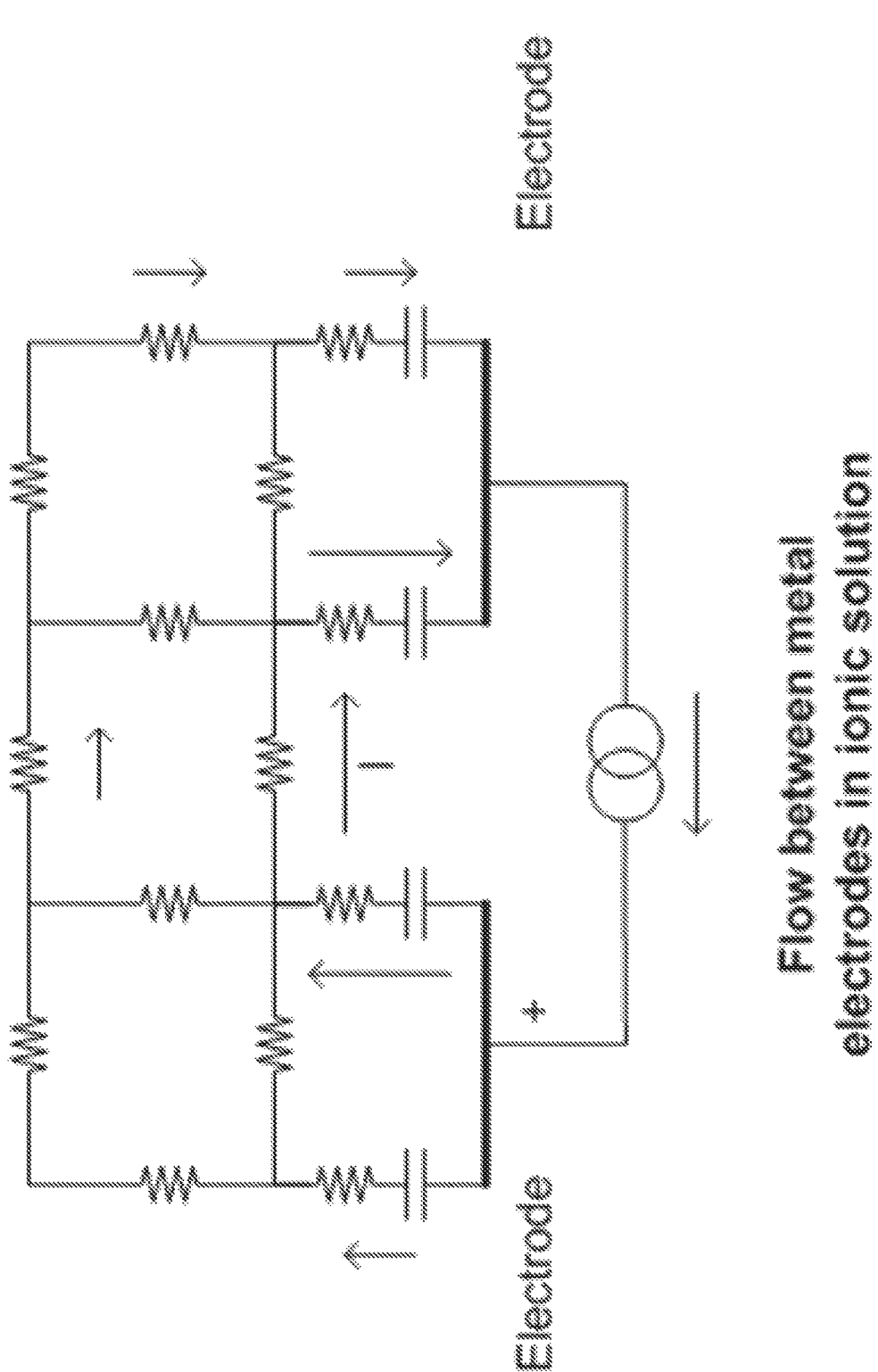
FIG. 11B illustrates a model of a metal electrode in a conductive solution.

A similar effect happens when current flows between two electrodes, as shown in FIG. 11B. During application of a stimulus, the current preferentially flows between the parts of the electrodes where they are closest. When the current is interrupted, the charge on the surface of the electrodes must re-equilibrate; this also leads to a residual current and contributes to electrode artefact seen by a sense electrode.

Figure 12A:
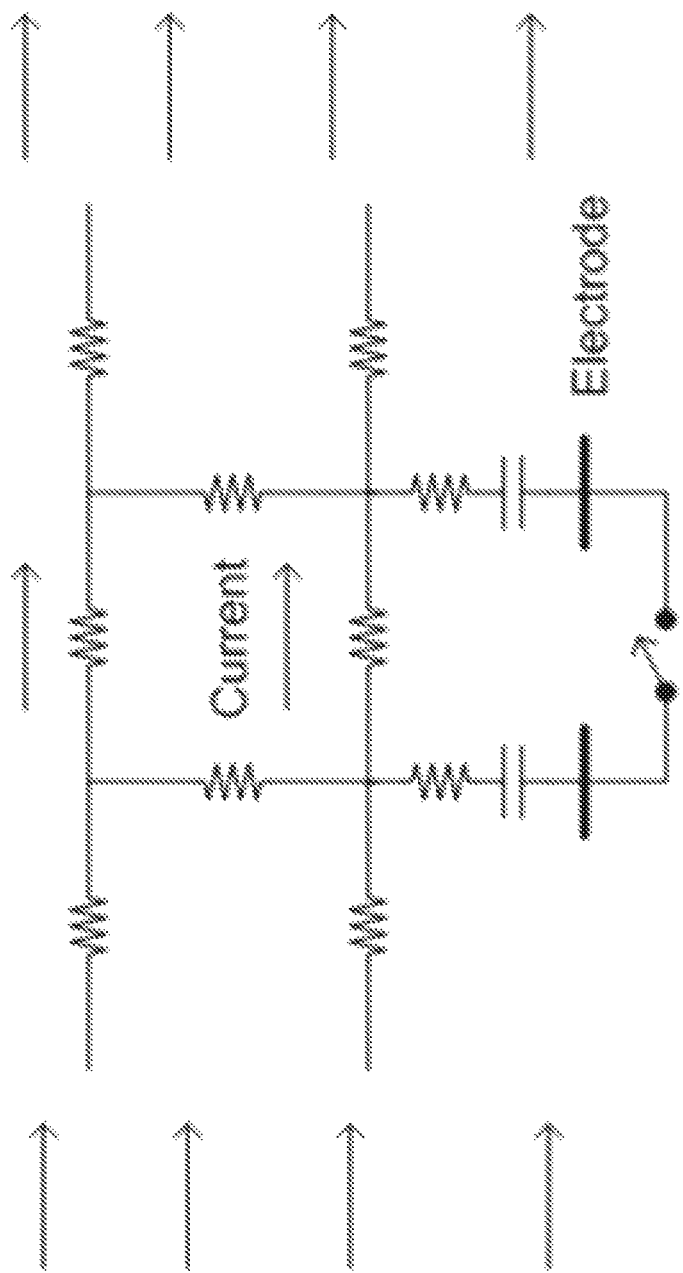
FIG. 12A illustrates segmented sense electrode which may be used to reduce artefact without sacrificing noise, impedance or current carrying capacity.
Figure 12B:
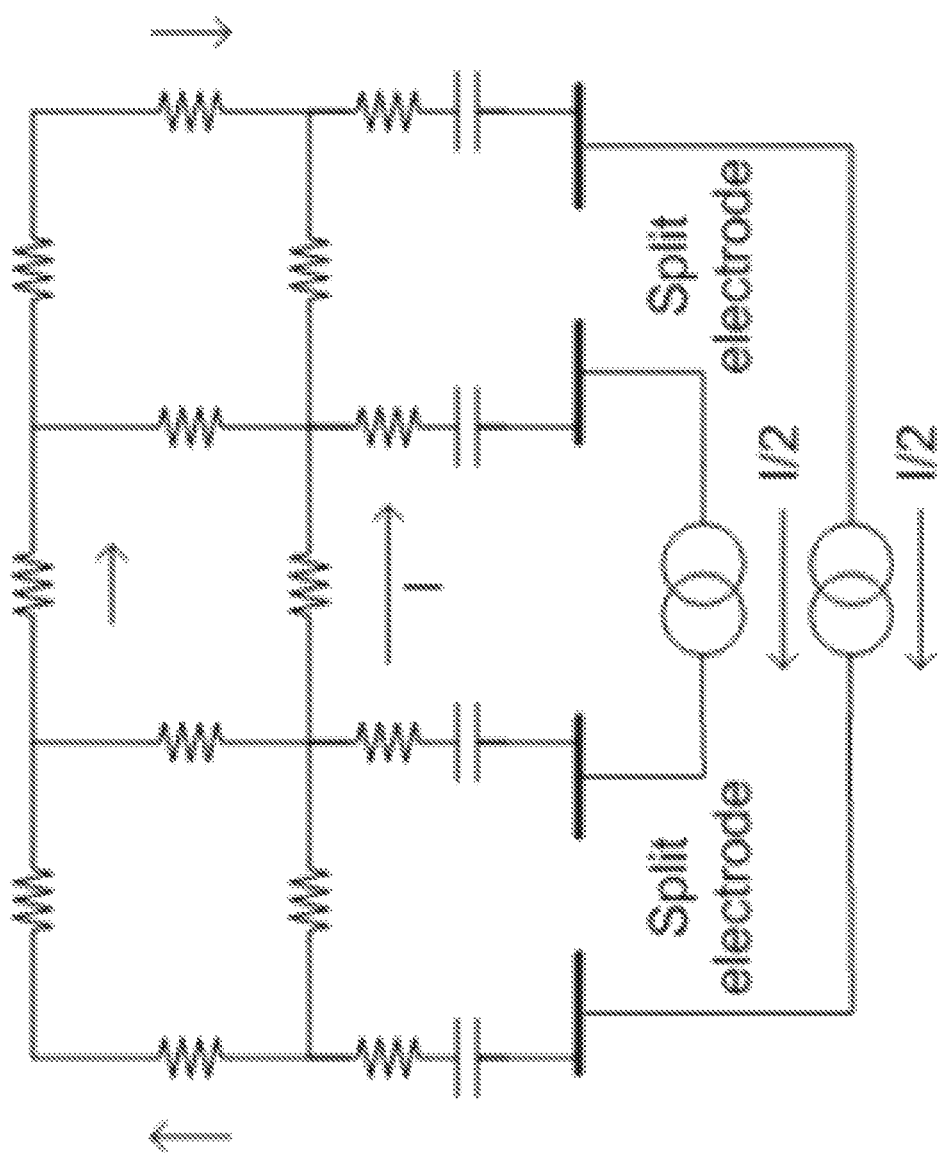
FIG. 12B illustrates a segmented drive electrode which may be used to reduce artefact without sacrificing noise, impedance or current carrying capacity.

The model of FIG. 11 predicts that using smaller electrodes will reduce artefact. However, smaller electrodes will have higher noise when used as measurement electrodes, and higher resistance and lower current carrying capacity when used as stimulus electrodes. Two means to reduce artefact without sacrificing noise, impedance or current carrying capacity are shown in FIG. 12A and FIG. 12B. The electrode configuration of FIG. 12A reduces artefact induced in a single metallic electrode; the electrode is composed of two or more smaller electrodes that can be disconnected during a stimulation phase, and reconnected during a measurement phase. In the configuration of FIG. 12B, an electrode is segmented, and individual current sources are provided for each segment. This forces the current in the segments to match, and so reduces artefact.

The evoked response telemetry of the present invention may in some embodiments be used to monitor the effect of a delivered compound. The administration of compounds (drugs or other chemical therapeutics) to effect a change in the nervous system is common for treatment of a wide number of diseases and disorders. Anaesthetics of various types are administered to the spinal cord for the relief of pain. Perhaps the most common form is administration of anaesthetics in the epidural space for pain relief during child birth.

In such embodiments, a catheter comprising a drug delivery tube may be fitted with electrode elements and configured to obtain neural response measurements in accordance with the present invention in order to monitor drug-induced effects on the neural response. Alternatively an electrode array may be temporarily or permanently implanted and used to apply neural stimuli and monitor the neural response. The neural response measurements may be obtained repeatedly during administration of the drug in order to directly measure the effect of the administered drug and control the dosage delivered.

Figure 13A:
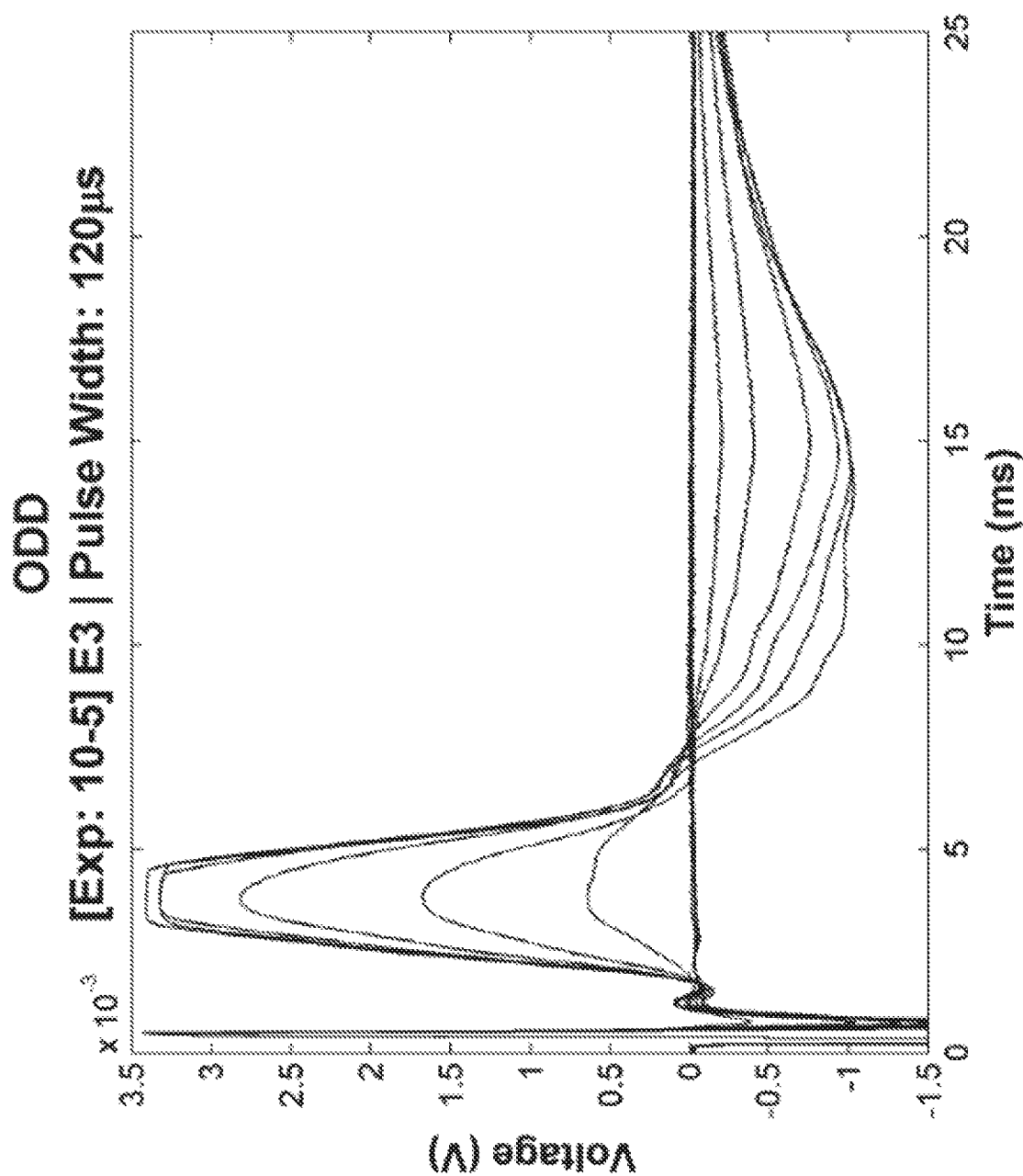
FIG. 13A and FIG. 13B illustrate the effect of epidural administration of Lignocaine on suppression of the spinal evoked responses.
Figure 13B:
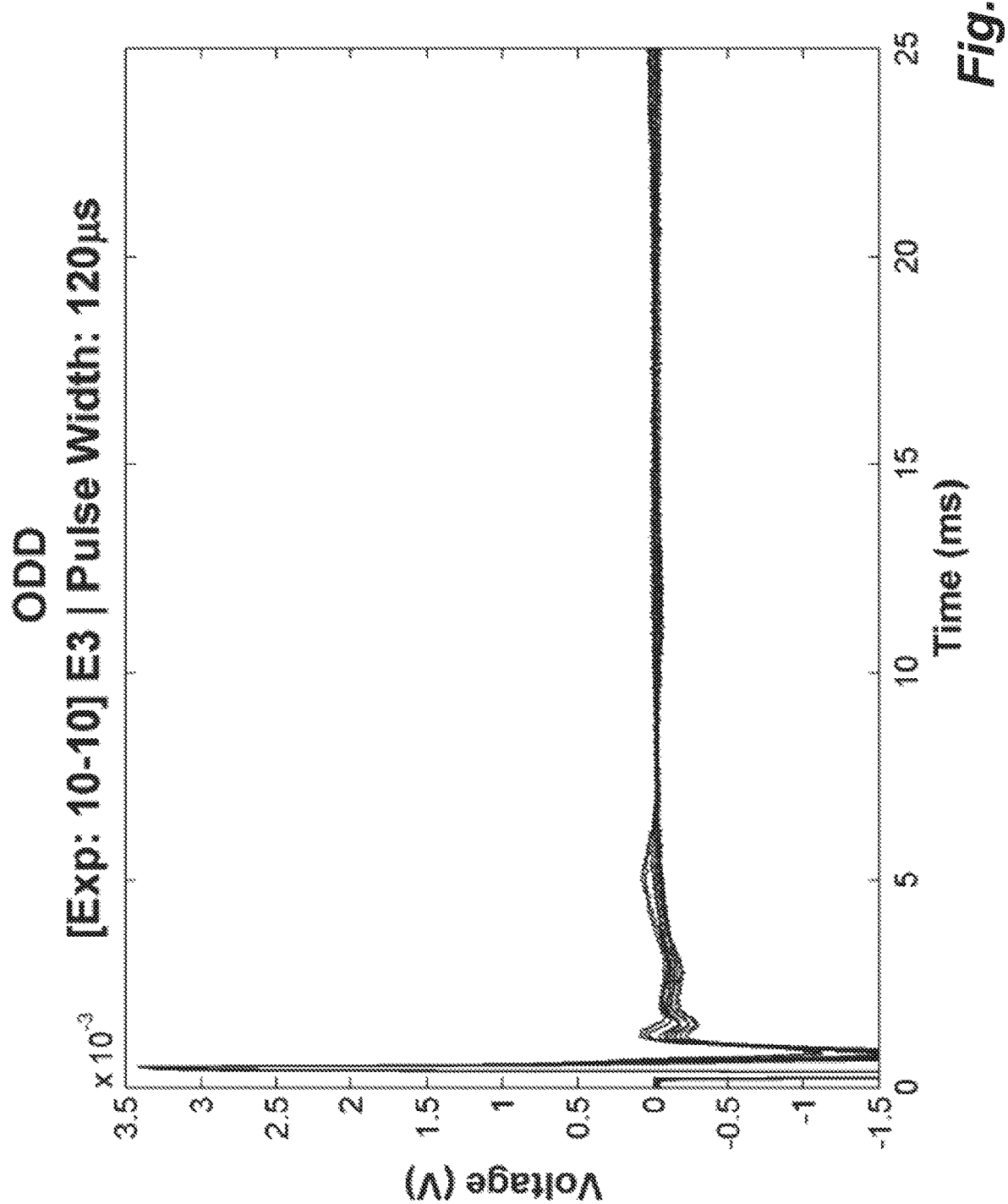

FIG. 13A and FIG. 13B illustrate the effect of administration of anaesthetic to the spinal cord, with a neural response being present prior to administration and largely being absent subsequent to administration. As can be seen, there is a direct correlation between the measured evoked response and the dosage of the anaesthetic. A "partial block" may be effected by ceasing administration of the anaesthetic once the neural response amplitude reduces to a desired level. The technology described herein is suitable for full implantation within the body of a subject and as a result the evoked potential monitoring could be used in the administration of an active compound to produce a therapeutic benefit. The system could be integrated within an implantable pump to control the administration of the compound.

Figure 14A:
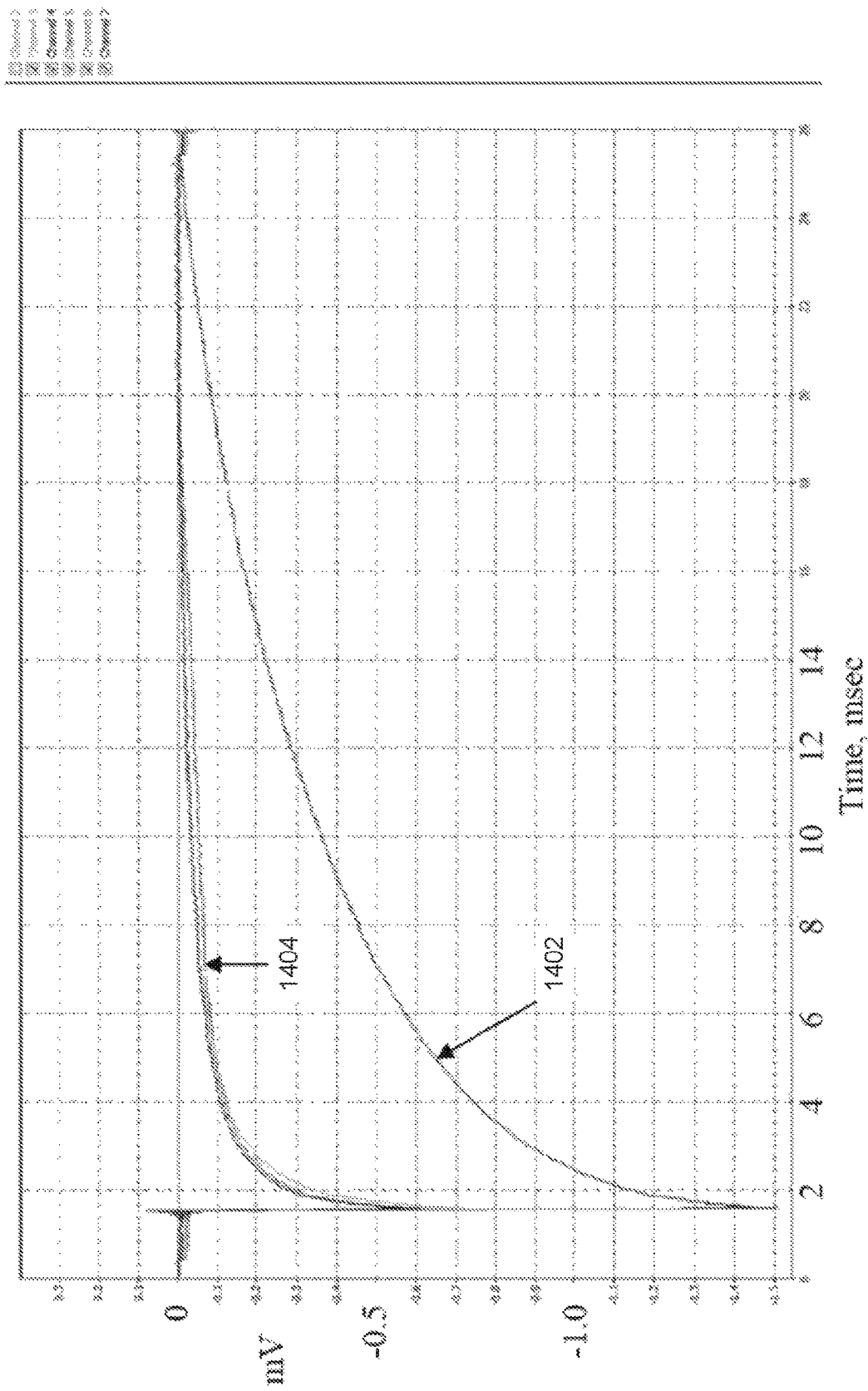
FIG. 14A is a plot showing the artefact arising when electrode shorting is performed.
Figure 14B:
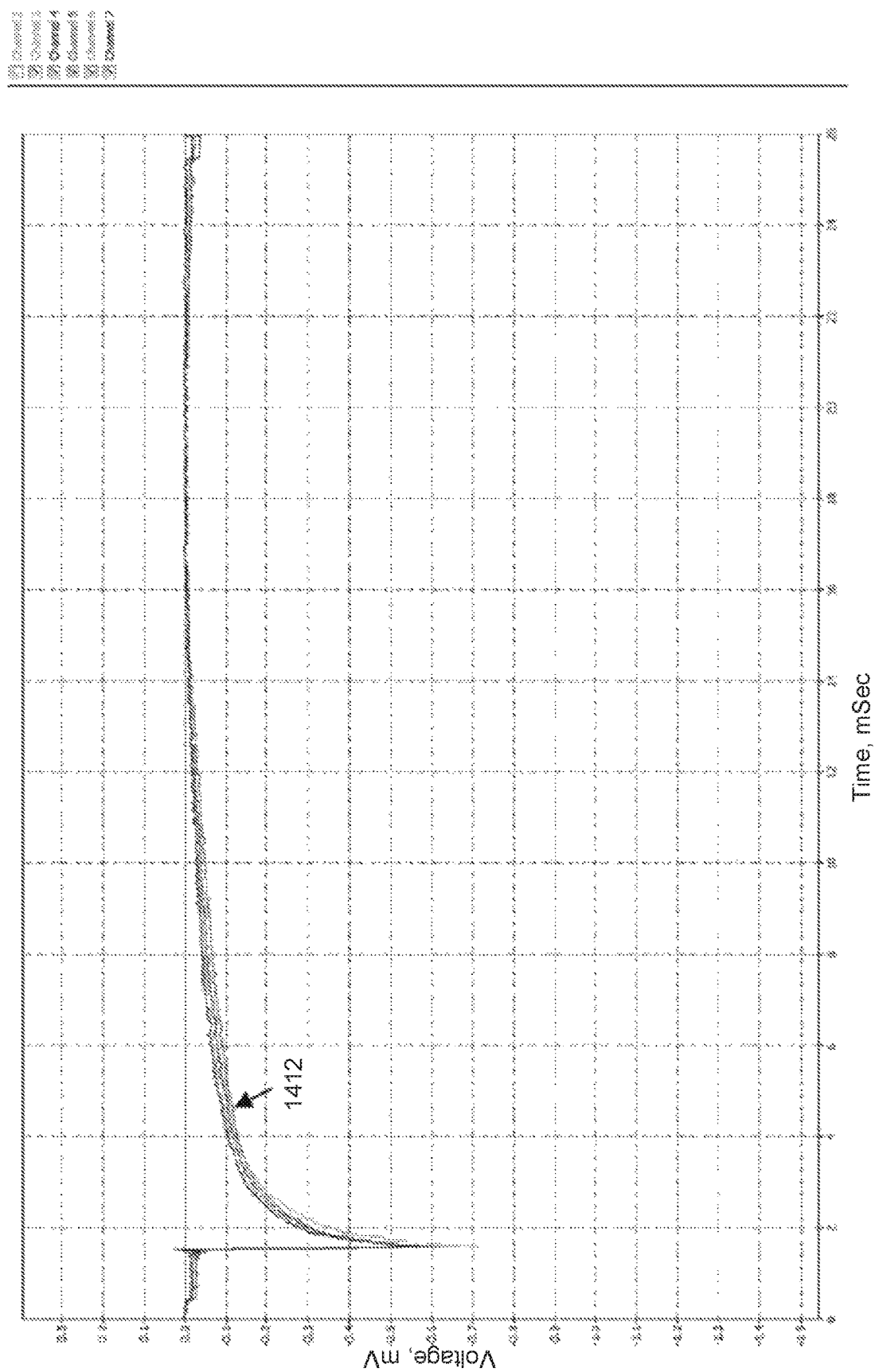
FIG. 14B is a plot showing the artefact arising when the sense electrode is disconnected from the measurement circuitry and from the stimulus electrodes after the stimulus.

FIG. 14A and FIG. 14B shows two plots which compare the artefact arising when electrode shorting is performed, to the artefact arising when the sense electrode is disconnected from the measurement circuitry and from the stimulus electrodes after the stimulus.

The plots of FIG. 14 were obtained from an array placed in a saline bath, and were taken under the following conditions. A stimulation comprising a biphasic pulse of amplitude 10 mA and duration 400 μs was applied using a tripolar configuration, with electrodes E1 and E3 grounded and electrode E2 stimulating, at a stimulus rate of 40 Hz. The artefact measurement of interest (1402, 1412) was obtained on electrode 4 for each plot. Measurements were also obtained on electrodes 5 to 7 using the method of the present invention in both plots, these measurements indicated collectively at 1404, 1412. The measurement parameters for each plot included recovering charge on the stimulus electrodes by short circuiting the stimulus electrodes to each other for 100 μs before stimulation. As shown in FIG. 14A, when the sense electrodes were shorted as taught by prior art methods, the artefact in the measurement 1402 was considerably larger than the artefact present in measurements 1404. In contrast, when the sense electrode E4 was disconnected from the measurement circuitry and from the stimulus electrodes after the stimulus, as taught by the present invention, the artefact in the measurement 1412 from electrode E4 was considerably reduced. The effect of this benefit in preferred embodiments is that an evoked response can be recorded in a single measurement with sufficient signal to noise ratio to permit analysis of the individual evoked response measurement. Moreover, such "single shot" measurements can in some embodiments be obtained in response to normal therapeutic stimuli. This avoids wasting battery power to deliver a train of high power stimuli having parameters which are well outside normal therapeutic settings and thus not of therapeutic benefit, to enable an averaged response to be extracted over a large number of measurements, as is required in systems having poor artefact performance.

It will be appreciated by persons skilled in the art that numerous variations and/or modifications may be made to the invention as shown in the specific embodiments without departing from the spirit or scope of the invention as broadly described. For example in the measurements stages of charge recovery (FIG. 2B), stimulate (FIG. 2C) and delay (FIG. 2D), the sense electrodes are described as being disconnected from the sense circuitry. In the embodiment of FIG. 2 this is effected by setting the sample and hold 208 to "hold", and it is noted that in alternative embodiments the sample and hold 208 may be positioned elsewhere in the measurement chain. Such embodiments are all to be understood to be within the scope of the phrase "disconnecting the sense electrode from the measurement circuitry" or similar as used herein. The present embodiments are, therefore, to be considered in all respects as illustrative and not restrictive.

The invention claimed is:

1. A method of measuring a neural response evoked by a stimulus, the method comprising:
    applying the stimulus to neural tissue;
    during the applying of the stimulus, disconnecting electrode segments of a sense electrode so as to limit disequilibrium arising on the sense electrode to each of the electrode segments; and
    measuring a neural response evoked by the stimulus in a neural signal sensed at the sense electrode by connecting the electrode segments to each other, and connecting the sense electrode to measurement circuitry.

2. The method of claim 1, wherein the measuring a neural response is a single-ended measurement obtained by passing a signal from the sense electrode to a single-ended amplifier.

3. The method of claim 1, wherein the measuring a neural response is a differential measurement obtained by passing signals from two additional sense electrodes to a differential amplifier, each sense electrode of the two additional sense electrodes comprising at least two respective electrode segments.

4. The method of claim 1, further comprising obtaining a curve of an averaged measurement vs. stimulus amplitude in order to obtain information regarding recruitment effected by the stimulus.

5. The method of claim 1, wherein the measuring a neural response is used for feedback control by an implanted neurostimulator.

6. The method of claim 1, when applied contemporaneously with administration of a drug, in order to gauge efficacy of drug delivery.

7. The method of claim 6, wherein drug delivery is controlled by feedback based on compound action potential (CAP) measurements.

8. The method of claim 1, wherein the CAP is recorded within approximately 3 cm of a stimulus site.

9. An implantable device for measuring a neural response evoked by a stimulus, the implantable device comprising:
- a plurality of electrodes including one or more stimulus electrodes and one or more sense electrodes, wherein at least one of the one or more sense electrodes comprises at least two sense electrode segments;
- one or more stimulus sources for providing the stimulus to be delivered from the one or more stimulus electrodes to neural tissue;
- measurement circuitry for amplifying a neural signal sensed at the one or more sense electrodes; and
- a control unit configured to:
  - disconnect the at least two sense electrode segments during delivery of the stimulus, so as to limit disequilibrium arising on the at least one of the one or more sense electrodes to each sense electrode segment of the at least two sense electrode segments;
  - control the one or more stimulus sources to provide the stimulus to be delivered to the neural tissue;
  - connect the at least two sense electrode segments to each other and connect the at least one of the one or more sense electrodes to the measurement circuitry; and
  - measure the neural response evoked by the stimulus in the amplified neural signal.

10. The implantable device of claim 9,
wherein at least one of the one or more stimulus electrodes comprises at least two stimulus electrode segments,
wherein the control unit is configured to drive the at least two stimulus electrode segments by distinct respective stimulus sources of the one or more stimulus sources,
wherein the stimulus delivered from the at least one of the one or more stimulus electrode is a sum of contributions of the distinct respective stimulus sources, and
wherein a disequilibrium arising on the at least one of the one or more stimulus electrode during delivery of the stimulus is limited to each stimulus electrode segment of the at least two stimulus electrode segments.

* * * * *